(12) United States Patent
Wannamaker et al.

(10) Patent No.: US 9,994,613 B2
(45) Date of Patent: *Jun. 12, 2018

(54) PRODRUG OF AN ICE INHIBITOR

(71) Applicant: VERTEX PHARMACEUTICALS INCORPORATED, Cambridge, MA (US)

(72) Inventors: Marion W. Wannamaker, Bolton, MA (US); Robert J. Davies, Arlington, MA (US)

(73) Assignee: Vertex Pharmaceuticals Incorporated, Cambridge, MA (US)

(*) Notice: Subject to any disclaimer, the term of this patent is extended or adjusted under 35 U.S.C. 154(b) by 0 days. days.

This patent is subject to a terminal disclaimer.

(21) Appl. No.: 15/288,863

(22) Filed: Oct. 7, 2016

(65) Prior Publication Data
US 2017/0022249 A1    Jan. 26, 2017

Related U.S. Application Data

(60) Continuation of application No. 14/747,578, filed on Jun. 23, 2015, now Pat. No. 9,487,555, which is a continuation of application No. 13/709,610, filed on Dec. 10, 2012, now Pat. No. 9,156,880, which is a division of application No. 13/210,712, filed on Aug. 16, 2011, now Pat. No. 8,329,662, which is a division of application No. 12/165,838, filed on Jul. 1, 2008, now Pat. No. 8,022,041, which is a division of application No. 09/860,750, filed on May 18, 2001, now Pat. No. 7,417,029.

(60) Provisional application No. 60/205,439, filed on May 19, 2000.

(51) Int. Cl.
| | |
|---|---|
| *C07K 5/062* | (2006.01) |
| *A61K 38/00* | (2006.01) |
| *A61P 17/00* | (2006.01) |
| *C07K 5/06* | (2006.01) |
| *C07D 307/02* | (2006.01) |
| *C07D 477/02* | (2006.01) |
| *C07D 477/20* | (2006.01) |
| *C07K 5/02* | (2006.01) |
| *C07K 5/08* | (2006.01) |
| *C07D 207/16* | (2006.01) |
| *C07K 5/083* | (2006.01) |

(52) U.S. Cl.
CPC ........ *C07K 5/06034* (2013.01); *C07D 207/16* (2013.01); *C07D 307/02* (2013.01); *C07D 477/02* (2013.01); *C07D 477/20* (2013.01); *C07K 5/0202* (2013.01); *C07K 5/0205* (2013.01); *C07K 5/06* (2013.01); *C07K 5/06008* (2013.01); *C07K 5/06191* (2013.01); *C07K 5/08* (2013.01); *C07K 5/0808* (2013.01); *A61K 38/00* (2013.01)

(58) Field of Classification Search
CPC .... A61K 38/00; C07D 477/02; C07D 477/20; C07D 307/02; C07D 207/16; C07K 5/0202; C07K 5/0205; C07K 5/06034; C07K 5/06191; C07K 5/08; C07K 5/06008; C07K 5/06; C07K 5/0808
See application file for complete search history.

(56) References Cited

U.S. PATENT DOCUMENTS

| | | | |
|---|---|---|---|
| 4,465,679 | A | 8/1984 | Huang et al. |
| 5,008,245 | A | 4/1991 | Digenis et al. |
| 5,055,451 | A | 10/1991 | Krantz et al. |
| 5,158,936 | A | 10/1992 | Krantz et al. |
| 5,411,985 | A | 5/1995 | Bills et al. |
| 5,416,013 | A | 5/1995 | Black et al. |
| 5,430,128 | A | 7/1995 | Chapman et al. |

(Continued)

FOREIGN PATENT DOCUMENTS

| | | |
|---|---|---|
| AU | 64514/94 A | 12/1994 |
| EP | 0135349 A1 | 3/1985 |

(Continued)

OTHER PUBLICATIONS

"Chromatography" Kirk-Othmer Encyclopedia of Chemical Technology (published online Jan. 25, 2002 by John Wiley & Sons, Inc.

(Continued)

*Primary Examiner* — Julie Ha
*Assistant Examiner* — Li N Komatsu
(74) *Attorney, Agent, or Firm* — Pepper Hamilton LLP

(57) ABSTRACT

This invention describes an ICE inhibitor prodrug (I) having good bioavailability.

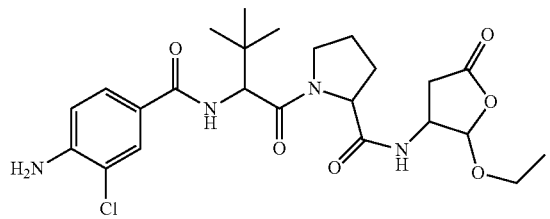

Compound I is useful for treating IL-1 mediated diseases such as rheumatoid arthritis, inflammatory bowel disease, Crohn's disease, ulcerative colitis, inflammatory peritonitis, septic shock, pancreatitis, traumatic brain injury, organ transplant rejection, osteoarthritis, asthma, psoriasis, Alzheimer's disease, myocardial infarction, congestive heart failure, Huntington's disease, atherosclerosis, atopic dermatitis, leukemias and related disorders, myelodysplastic syndrome, uveitis or multiple myeloma.

27 Claims, No Drawings

(56) References Cited

U.S. PATENT DOCUMENTS

| | | |
|---|---|---|
| 5,434,248 A | 7/1995 | Chapman et al. |
| 5,462,939 A | 10/1995 | Dolle et al. |
| 5,463,124 A | 10/1995 | Jacobi et al. |
| 5,486,623 A | 1/1996 | Zimmerman et al. |
| 5,498,616 A | 3/1996 | Mallamo et al. |
| 5,498,695 A | 3/1996 | Daumy et al. |
| 5,519,113 A | 5/1996 | Jendralla et al. |
| 5,552,400 A | 9/1996 | Dolle et al. |
| 5,565,430 A | 10/1996 | Dolle et al. |
| 5,585,357 A | 12/1996 | Dolle et al. |
| 5,585,486 A | 12/1996 | Dolle et al. |
| 5,639,745 A | 6/1997 | Dolle et al. |
| 5,656,627 A | 8/1997 | Bemis et al. |
| 5,670,494 A | 9/1997 | Dolle et al. |
| 5,710,153 A | 1/1998 | Ohmoto et al. |
| 5,716,929 A | 2/1998 | Bemis et al. |
| 5,744,451 A | 4/1998 | Allen et al. |
| 5,756,466 A | 5/1998 | Bemis et al. |
| 5,817,848 A | 10/1998 | Kamer et al. |
| 5,843,904 A | 12/1998 | Bemis et al. |
| 5,847,135 A | 12/1998 | Bemis et al. |
| 5,869,519 A | 2/1999 | Karanewsky et al. |
| 5,874,424 A | 2/1999 | Batchelor et al. |
| 5,877,197 A | 3/1999 | Karanewsky et al. |
| 5,919,790 A | 7/1999 | Allen et al. |
| 5,973,111 A | 10/1999 | Bemis et al. |
| 6,054,487 A | 4/2000 | Sekut et al. |
| 6,136,834 A | 10/2000 | Ohmoto et al. |
| 6,184,210 B1 | 2/2001 | Keana et al. |
| 6,184,244 B1 | 2/2001 | Karanewsky et al. |
| 6,187,771 B1 | 2/2001 | Karanewsky et al. |
| 6,197,750 B1 | 3/2001 | Karanewsky et al. |
| 6,204,261 B1 | 3/2001 | Batchelor et al. |
| 6,225,288 B1 | 5/2001 | Han et al. |
| 6,235,899 B1 | 5/2001 | Bouchet et al. |
| 6,242,422 B1 | 6/2001 | Karanewsky et al. |
| 6,258,948 B1 | 7/2001 | Batchelor et al. |
| 6,265,380 B1 | 7/2001 | Tung et al. |
| 6,268,207 B1 | 7/2001 | Bailey |
| 6,268,365 B1 | 7/2001 | Betageri et al. |
| 6,316,415 B1 | 11/2001 | Albrecht et al. |
| 6,323,180 B1 | 11/2001 | Llinas-brunet et al. |
| 6,329,379 B1 | 12/2001 | Llinas-brunet et al. |
| 6,329,417 B1 | 12/2001 | Llinas-brunet et al. |
| 6,376,484 B1 | 4/2002 | Ohmoto et al. |
| 6,410,531 B1 | 6/2002 | Llinas-brunet et al. |
| 6,420,380 B2 | 7/2002 | Llinas-brunet et al. |
| 6,420,522 B1 | 7/2002 | Bemis et al. |
| 6,423,840 B1 | 7/2002 | Batchelor et al. |
| 6,495,522 B1 | 12/2002 | Wang et al. |
| 6,531,474 B1 | 3/2003 | Wannamaker et al. |
| 6,534,523 B1 | 3/2003 | Llinas-brunet et al. |
| 6,617,309 B2 | 9/2003 | Tung et al. |
| 6,620,782 B1 | 9/2003 | Cai et al. |
| 6,632,962 B2 | 10/2003 | Golec et al. |
| 6,689,784 B2 | 2/2004 | Bebbington et al. |
| 6,699,856 B2 | 3/2004 | Han et al. |
| 6,716,818 B2 | 4/2004 | Cai et al. |
| 6,800,619 B2 | 10/2004 | Charrier et al. |
| 6,844,363 B2 | 1/2005 | Murakami et al. |
| 6,846,806 B2 | 1/2005 | Priestley |
| 6,909,000 B2 | 6/2005 | Farmer et al. |
| 6,939,854 B2 | 9/2005 | Priestley |
| 7,109,357 B2 | 9/2006 | Wannamaker et al. |
| 7,358,273 B2 | 4/2008 | Wannamaker et al. |
| 7,381,827 B2 | 6/2008 | Tanoury et al. |
| 7,417,029 B2 | 8/2008 | Wannamaker et al. |
| 7,652,153 B2 | 1/2010 | Charrier et al. |
| 7,834,200 B2 | 11/2010 | Tanoury et al. |
| 8,022,041 B2 | 9/2011 | Wannamaker et al. |
| 8,293,929 B2 | 10/2012 | Tanoury et al. |
| 8,329,662 B2 | 12/2012 | Wannamaker et al. |
| 8,691,848 B2 | 4/2014 | Wannamaker et al. |
| 9,156,880 B2 | 10/2015 | Wannamaker et al. |
| 9,487,555 B2 | 11/2016 | Wannamaker et al. |
| 2002/0016321 A1 | 2/2002 | Karanewsky et al. |
| 2002/0045623 A1 | 4/2002 | Charrier et al. |
| 2002/0058630 A1 | 5/2002 | Charrier et al. |
| 2002/0061853 A1 | 5/2002 | Golec |
| 2002/0147171 A1 | 10/2002 | Fritz et al. |
| 2002/0169177 A1 | 11/2002 | Kay et al. |
| 2003/0092703 A1 | 5/2003 | Mortimore et al. |
| 2003/0096737 A1 | 5/2003 | Diu-Hercend et al. |
| 2003/0119748 A1 | 6/2003 | Karanewsky et al. |
| 2003/0119899 A1 | 6/2003 | Wannamaker et al. |
| 2003/0162993 A1 | 8/2003 | Mortimore et al. |
| 2003/0236242 A1 | 12/2003 | Perni et al. |
| 2004/0009966 A1 | 1/2004 | Wos et al. |
| 2004/0014753 A1 | 1/2004 | O'Neil et al. |
| 2004/0019017 A1 | 1/2004 | Mortimore et al. |
| 2004/0019612 A1 | 1/2004 | Tyra et al. |
| 2004/0048797 A1 | 3/2004 | Miller et al. |
| 2004/0072850 A1 | 4/2004 | Knegtel et al. |
| 2004/0142876 A1 | 7/2004 | Colarusso et al. |
| 2004/0242494 A1 | 12/2004 | Brenchley et al. |
| 2004/0254117 A9 | 12/2004 | Saksena et al. |
| 2005/0209162 A1 | 9/2005 | Roy et al. |
| 2005/0233979 A1 | 10/2005 | Charrier et al. |
| 2005/0267101 A1 | 12/2005 | Randle |
| 2013/0066083 A1 | 3/2013 | Tanoury et al. |

FOREIGN PATENT DOCUMENTS

| | | |
|---|---|---|
| EP | 0410411 A2 | 1/1991 |
| EP | 0417721 A2 | 3/1991 |
| EP | 0519748 A2 | 12/1992 |
| EP | 0525420 A1 | 2/1993 |
| EP | 0528487 A2 | 2/1993 |
| EP | 0529713 A2 | 3/1993 |
| EP | 0533226 A1 | 3/1993 |
| EP | 0533350 A1 | 3/1993 |
| EP | 0547699 A1 | 6/1993 |
| EP | 0618223 A2 | 10/1994 |
| EP | 0623592 A1 | 11/1994 |
| EP | 0623606 A2 | 11/1994 |
| EP | 0644197 A1 | 3/1995 |
| EP | 0644198 A1 | 3/1995 |
| EP | 0810221 A1 | 12/1997 |
| EP | 1064298 B1 | 10/2008 |
| EP | 2011800 A2 | 1/2009 |
| EP | 1286989 B1 | 2/2012 |
| EP | 1396492 B1 | 2/2012 |
| EP | 2399915 B1 | 12/2014 |
| EP | 1725548 B1 | 1/2015 |
| EP | 2270005 B1 | 7/2015 |
| GB | 2292149 A | 2/1996 |
| JP | 9-165360 | 6/1997 |
| WO | WO 1991/015577 A1 | 10/1991 |
| WO | WO 1993/005071 A1 | 3/1993 |
| WO | WO 1993/009135 A1 | 5/1993 |
| WO | WO 1993/012076 A1 | 6/1993 |
| WO | WO 1993/014777 A1 | 8/1993 |
| WO | WO 1993/016710 A1 | 9/1993 |
| WO | WO 1994/000154 A1 | 1/1994 |
| WO | WO 1994/003480 A1 | 2/1994 |
| WO | WO 1995/000160 A1 | 1/1995 |
| WO | WO 1995/005192 A1 | 2/1995 |
| WO | WO 1995/026958 A1 | 10/1995 |
| WO | WO 1995/029672 A1 | 11/1995 |
| WO | WO 1995/030680 A1 | 11/1995 |
| WO | WO 1995/031535 A1 | 11/1995 |
| WO | WO 1995/035308 A1 | 12/1995 |
| WO | WO 1995/035367 A1 | 12/1995 |
| WO | WO 1996/003982 A1 | 2/1996 |
| WO | WO 1996/004647 A1 | 2/1996 |
| WO | WO 1996/025408 A1 | 8/1996 |
| WO | WO 1996/030395 A2 | 10/1996 |
| WO | WO 1996/033209 A1 | 10/1996 |
| WO | WO 1997/007805 A1 | 3/1997 |
| WO | WO 1997/008174 A1 | 3/1997 |
| WO | WO 1997/022619 A | 6/1997 |
| WO | WO 1997/024339 A1 | 7/1997 |
| WO | WO 1998/001133 A1 | 1/1998 |
| WO | WO 1998/004539 A1 | 2/1998 |

(56) References Cited

FOREIGN PATENT DOCUMENTS

| | | |
|---|---|---|
| WO | WO 1998/010778 A1 | 3/1998 |
| WO | WO 1998/011109 A1 | 3/1998 |
| WO | WO 1998/011129 A1 | 3/1998 |
| WO | WO 1998/016502 A1 | 4/1998 |
| WO | WO 1998/016505 A1 | 4/1998 |
| WO | WO 1998/049189 A1 | 11/1998 |
| WO | WO 1999/003852 A1 | 1/1999 |
| WO | WO 1999/036426 A1 | 1/1999 |
| WO | WO 1999/047545 A2 | 9/1999 |
| WO | WO 2000/055114 A1 | 9/2000 |
| WO | WO 2000/055127 A1 | 9/2000 |
| WO | WO 2000/061542 A1 | 10/2000 |
| WO | WO 2001/005772 A1 | 1/2001 |
| WO | WO 2001/010383 A2 | 2/2001 |
| WO | WO 2001/016093 A1 | 3/2001 |
| WO | WO 2001/042216 A2 | 6/2001 |
| WO | WO 2001/072707 A2 | 10/2001 |
| WO | WO 2001/081330 A | 11/2001 |
| WO | WO 2001/081331 A1 | 11/2001 |
| WO | WO 2001/090063 A2 | 11/2001 |
| WO | WO 2001/090070 A1 | 11/2001 |
| WO | WO 2001/094351 A1 | 12/2001 |
| WO | WO 2002/042278 A2 | 5/2002 |
| WO | WO 2002/094263 A2 | 11/2002 |
| WO | WO 2003/042169 A2 | 5/2003 |
| WO | WO 2003/068242 A1 | 8/2003 |
| WO | WO 2003/088917 A2 | 10/2003 |
| WO | WO 2003/103677 A1 | 12/2003 |
| WO | WO 2003/104231 A1 | 12/2003 |
| WO | WO 2003/106460 A1 | 12/2003 |
| WO | WO 2004/002961 A1 | 1/2004 |
| WO | WO 2004/058718 A1 | 7/2004 |
| WO | WO 2004/106304 A2 | 12/2004 |
| WO | WO 2005/090334 A2 | 9/2005 |

OTHER PUBLICATIONS

Abstract of Aibe, K., WO 98/01133, issued Jan. 1998.
Abstract of Ando, R., WO 96/25408, issued Aug. 1996.
Abstract of Ando, R., WO 98/04539, issued Feb. 1998.
Abstract of Ohmoto, K., WO 97/24339, issued Jul. 1997.
Alcocer-Valera et al. "Spontaneous production of, and defective response to interleukin-1 by peripheral blood mononuclear cells from patients with sceroderma" (1985) *Clin. Exp. Immunol.* 59:666-672.
Alnemri et al. "Cloning and Expression of Four-Novel Isoforms of Human Interkeukin-1β Converting Enzyme with Different apoptotic Activities" (Mar. 3, 1995) *J. Biol. Chem.* 270(9):4312-4317.
Ankersmit et al. "Increased serum concentrations of soluble CD95/Fas and caspase 1.ICE in patients with acute angina" (2004) *Heart* 90:151-154.
Anstee et al. "Impact of pan-caspase inhibition in animal models of established steatosis and non-alcoholic steatohepatitis" (2010) *J. Hepatol.*, doi:10.1016/j.jhep.2010.03.016.
Antonopoulos et al., "Functional caspase-1 is required for Langerhans cell migration and optimal contact sensitization in mice" (2001) *J. Immunol.* 166:3672-3677.
Arend et al. "Inhibition of the Production and Effects of Interleukin-1 and Tumor Necrosis Factor α in Rheumatoid Arthritis" (Feb. 1995) *Arthritis Rheum* 38(2):151-160.
Arndt et al. "Expression of Interleukin-18 in the Lung after Endotoxemia or Hemorrhage-Induced Acute Lung Injury" (2000) *Am. J. Respir. Cell Mol. Biol.* 22:708-713.
Ashkenazi et al. "Death Receptors: Signaling and Modulation" (Aug. 28, 1998) *Science* 281(5381):1305-1308.
Ator "Peptide and Non-peptide Inhibitors of Interleukin-1β Converting Enzyme" (1994) Cambridge Healthtech Institute (Inflammatory Cytokine Antagonists Targets, Strategies, and Indication), pp. 1-15.

Ator et al. "Interleukin-1β Converting Enzyme: Biology and the Chemistry of Inhibitors" (1995) *Curr. Pharm. Design* 1:191-210.
Bani "Effect of Interleukin-1-beta on Metastasis Formation in Different Tumor Systems" (Jan. 16, 1991) *J. Natl. Cancer Inst.* 83(2):119-123.
Barinaga "Is Apoptosis Key in Alzheimer's Disease?" (Aug. 28, 1998) *Science* 281(5381):1303-1304.
Barinaga "Stroke-Damaged Neurons May Commit Cellular Suicide" (Aug. 28, 1998) *Science* 281(5381):1302-1303.
Bataille et al. "The critical role of interleukin-6, interleukin-IB and macrophage colony-stimulating factor in the pathogenesis of bone lesions in multiple myelmoma" (1992) *Int. J. Clin. Lab Res.* 21:283-287.
Bednarski et al. "Attenuation of Autoimmune Disease in Fas-Deficient Mice by Treatment with a Cytotoxic Benzodiazepine" (Mar. 2003) *Arthritis and Rheumatism* 48(3):757-766.
Belardelli "Role of Interferons and Other Cytokines in the Regulation of the Immune Response" (Mar. 1995) *APMIS* 103(3):161-179.
Bemis et al. "Preparation of Peptide Analogs as Inhibitors of Interleukin-1 Beta Converting Enzyme" (1996) *CAPLUS* 124:290273.
Black et al. "Activation of Interkeukin-1β by a Co-induced Protease" (Apr. 24, 1989) *FEBS Lett.* 247(2):386-390.
Brown et al. "Ruthenium Diphosphine Complexes for Catalysis; a General Synthesis and Direct Comparisons with Rhodium Complexes" (1995) *Recl. Trav. Chim. Pays-Bas* 114:242-251.
Burk et al. "Highly Regio- and Enantioselective Catalytic Hydrogenation of Enamides in Conjugated Diene Systems: Synthesis and Application of γ, δ-Unsaturated Amino Acids" (1998) *J. Amer. Chem. Soc.* 120:657-663.
Burk et al. "Preparation and Use of $C_2$-Symmetric Bis(Phospholanes): Production of α-Amino Acid Derivatives via Highly Enantioselective Hydrogenation Reactions" (1993) *J. Amer. Chem. Soc.* 115:10125-10138.
Car et al. "Interferon γ Receptor Deficient Mice are Resistant to Endotoxic Shock" (May 1, 1994) *J. Exp. Med.* 179(5):1437-1444.
Casano et al. "The Structure and Complete Nucleotide Sequence of the Murine Gene Encoding Interleukin-1β Converting Enzyme (ICE)" (Apr. 1994) *Genomics* 20(3):474-481.
Chapman "Synthesis of a Potent, Reversible Inhibitor of Interleukin-1β Converting Enzyme" (1992) *Bioorg. Med. Chem. Lett.* 2(6):613-618.
Dalton et al. "Multiple Defects of Immune Cell Function in Mice with Disrupted Interferon-Gamma Genes" (Apr. 1993) *Science* 259(5102):1739-1742.
Database Case Citation 2001:798211 (retrieved Mar. 11, 2010).
Dewhirst et al. "Purification and Partial Sequence of Human Osteoclast-activating Factor: Identity with Interleukin 1 beta" (Oct. 1, 1985) *J. Immunol.* 135(4):2562-2568.
Dinerello "Interleukin-18" (Sep. 1999) *Methods* 19(1):121-132.
Dolle et al. "Aspartyl .alpha.-((Diphenylphosphinyl)oxy)methyl Ketones as Novel Inhibitors of Interleukin-1β Converting Enzyme. Utility of the Diphenylphosphinic Acid Leaving Group for the Inhibition of Cystein Proteases" (1995) *J. Med. Chem.* 38:220-222.
Dolle et al. "Aspartyl α-((1-Phenyl-3-(trifluoromethyl)-pyrazol-5-yl)oxy)methyl Ketones as Interleukin-1β Converting Enzyme Inhibitors. Significance of the $P_1$ and $P_3$ Amido Nitrogens for Enzyme-Peptide Inhibitor Binding" (Nov. 11, 1994) *J. Med. Chem.* 37(23):3863-3865.
Dolle et al. "First Examples of Peptidomimetic Inhibitors of Interleukin-1β Converting Enzyme" (Jun. 21, 1996) *J. Med. Chem.* 39(13):2438-2440.
Dolle et al. "$P_1$ Aspartate-Based Peptide .alpha.((2,6-Dichlorobenzoyl)oxy)methyl Ketones as Potent Time-Dependent Inhibitors of Interleukin-1β-Converting Enzyme" (1994) *J. Med. Chem.* 37:563-564.
Dolle et al. "Pyridazinodiazepines as a High-Affinity, $P_2$-$P_3$ Peptidomimetic Class of Interleukin-1β-Converting Enzyme Inhibitor" (Jun. 20, 1997) *J. Med. Chem.* 40(13):1941-1946.
Duan et al. "ICE-LAP6, a Novel Member of the ICE/Ced-3 Gene Family, Is Activated by the Cytotoxic T Cell Protease Granzyme B" (Jul. 12, 1996) *J. Biol. Chem.* 271(34):16720-16724.

(56) References Cited

OTHER PUBLICATIONS

Edwards et al. "Design, Synthesis, and Kinetic Evaluation of a Unique Class of Elastase Inhibitors, the Peptidyl .alpha.-Ketobenzoxazoles, and the X-ray Crystal Structure of the Covalent Complex between Porcine Pancreatic Elastase and Ac-Ala-Pro-Val-2-Benzoxazole" (1992) *J. Am. Chem. Soc.* 114:1854-1863.
Elford et al. "Reduction of Inflammation and Pyrexia in the Rat by Oral Administration of SDZ 224-015, an Inhibitor of the Interleukin-1β Converting Enzyme" (1995) *Br. J. Pharmacology* 115:601-606.
Ellis et al. "Mechanisms and Functions of Cell Death" (1991) *Ann. Rev. Cell. Biol.* 7:663-698.
Endres et al. "Attenuation of Delayed Neuronal Death After Mild Focal Ischemia in Mice by Inhibition of the Caspase Family" (1998) *J. Cerebral Blood Flow and Metabolism* 18:238-247.
Escobar et al. "Pseudoesteres 3-Formilacrilicos Monohalogenados, Preparaction, Estructura Y Comportamiento En La Sintesis Dienica" (1971) *Ann. Quim.* 67:43-57 (with English abstract).
European Search Report and Written Opinion for EP10177537 dated Nov. 25, 2010.
European Search Report and Written Opinion for EP11178126 dated Nov. 21, 2011.
European Search Report for EP03020900 dated Jan. 13, 2004.
European Search Report for EP08017565 dated Apr. 29, 2009.
European Search Report for EP99912662 dated May 26, 2003.
Fan et al. "Stimulation of Angiogenesis by Substance P and Interleukin-1 in the Rat and its Inhibition by $NK_1$ or Interleukin-1 Receptor Antagonists" (1993) *Br. J. Pharmacol.* 110:43-49.
Fantuzzi et al. "Response to Local Inflammation of IL-1β-Converting Enzyme-Deficient Mice[1]" (1997) *J. Immunol.* 158:1818-1824.
Faucheu et al. "A novel human protease similar to the interleukin-1β converting enqyme induces apoptosis in transfected cells" (May 1, 1995) *EMBO J.* 14(9):1914-1922.
Fauszt et al. "Inhibition of Interleukin-1β Converting Enzyme by Peptide Derivatives" (1994) Proc. of the 13th Am. Peptide Symp, Jun. 20-25, 1993; Hodges, R.S. and Smith, J.A., Eds., Peptides, pp. 589-591.
Feringa et al. "Asymmetric 1,4-additions to 5-alkoxy-2(5H)-furanones. An Efficient synthesis of (R)- and (S)-3,4-epoxy-1-butanol" (1988) *Tetrahedron* 44(23):7213-7222.
Fernandes-Alnemri et al. "CPP32, a Novel Human Apoptotic Protein with Homology to *Caenorhabditis elegans* Cell Death Protein Ced-3 and Mammalian Interleukin-1β-converting Enzyme" (Dec. 9, 1994) *J. Biol. Chem.* 269(49):30761-30764.
Fernandes-Alnemri et al. "In vitro activation of CPP32 and Mch3 by Mch4, a novel human apoptotic cysteine protease containing two FADD-like domains" (Jul. 23, 1996) *PNAS* 93(15):7464-7469.
Fernandes-Alnemri et al. "McH2, a New Member of the Apoptotic Ced-3/Ice Cysteine Protease Gene Family" (Jul. 1, 1995) *Cancer Res.* 55(13):2737-2742.
Fernandes-Alnemri et al. "Mch3, a novel human apoptotic cysteine protease highly related to CPP32" (Deember 15, 1995) *Cancer Res.* 55(24):6045-6052.
Fletcher et al. "A Synthetic Inhibitor of Interleukin-1β Converting Enzyme Prevents Endotoxin-Induced Interleukin-1β Production in Vitro and in Vivo" (1995) *J. Interfer. Cytokine Res.* 15:243-248.
Frerot et al. "PyBOP®₁ and PyBroP: Two Reagents for the Difficult Coupling of the α, α-Dialkyl Amino Acid, Aib." (1991) *Tetrahedron* 47(2):259-270.
Friedlander et al. "Inhibition of ICE Slows ALS in Mice" (Apr. 9, 1997) *Nature* 388:31-32.
Furlan et al. "Caspase-1 Regulates the Inflammatory Process Leading to Autoimmune Demyelination" (1999) *J. Immunol.* 163:2403-2409.
Gagliardini et al. "Prevention of Vertebrate Neuronal Death by the crmA Gene" (Feb. 11, 1994) *Science* 263:826-828.
Gerig et al. "Attemped Synthesis of 2-Methylalanyl-L-prolyl-Ltryptophan an Unexpected Result" (1976) *J. Org. Chem.* 41(9):1653-1655.

Graybill et al. "Preparation and Evaluation of Peptidic Aspartyl Hemiacetals as Reversible Inhibitors of Interleukin-1β Converting Enzyme (ICE)" (1994) *Int. J. Peptide Protein Res.* 44(2): 173-182.
Graybill et al. "The Preparation and Evaluation of Peptidic Aspartyl Hemiacetals as Reversible Inhibitors of ICE" (1993) Am. Chem. Soc. Abs. (206th Natl. Mtg.), MEDI 235.
Green et al. "Mitochondria and Apoptosis" (Aug. 28, 1998) *Science* 281(5381):1309-1312.
Green et al. "Protective Groups in Organic Synthesis" (1999) 3rd edition, John Wiley & Sons, Inc. (TOC).
Grobmyer et al. "Peptidomimetic Fluoromethylketone Rescues Mice from Lethal Endotoxic Shock" (1999) *Molecular Medicine* 5:585-594.
Hanessian et al. "Design and Synthesis of a Prototype Model Antagonist of Tachykinin NK-2 Receptor" (1994) *Bioorg. Med. Chem. Lett.* 4(11):1397-1400.
Hara et al. "Inhibition of interleukin 1β converting enzyme family proteases reduces ischemic and excitotoxic neuronal damage" (Mar. 1997) *PNAS USA* 94:2007-2012.
Holly et al. "Caspase Inhibition Reduces Myocyte Cell Death Induced by Myocardial Ischemia and Reperfusion in Vivo" (1999) *J. Mol. Cell Cardiol.* 31:1709-1715.
Hotchkiss et al. "Caspase inhibitors improve survival in sepsis: a critical role of the lymphocyte" (Dec. 2000) *Nature Immunol.* 1(6):496-450.
Howard et al. "IL-1-converting enzyme requires aspartic acid residues for processing of the IL-1 beta precursor at two distinct sites and does not cleave 31-kDa IL-1 alpha" (Nov. 1, 1991) *J. Immunol.* 147(9):2964-2969.
Hu et al. "Caspase-14 is a Novel Developmentally Regulated Protease" (Nov. 6, 1998) *J. Biol. Chem.* 273(45):29648-29653.
Huang et al. "Immune response in mice that lack the interferon—gamma receptor" (Mar. 19, 1993) *Science* 259(5102):1742-1745.
Humke et al. "ERICE, a Novel FLICE-activatable Caspase" (Jun. 19, 1998) *J. Biol. Chem.* 273(25):15702-15707.
Ilzecka et al. "Interleukin-1β Converting Enzyme/Caspase 1 (ICE/Caspase-1) and Soluble APO-1/Fas/CD 95 Receptor in Amyotrophic Lateral Sclerosis Patients" (2001) *Acta Neurolog. Scand.* 103:255-258.
International Search Report and Written Opinion for PCT/US2005/008251 dated Sep. 9, 2005.
International Search Report for PCT/US1999/005919 dated Oct. 12, 1999.
International Search Report for PCT/US2001/016441 dated Nov. 21, 2001.
Jandiski "Osteoclast activating factor is now interleukin-1 beta: historical perspective and biological implications" (Apr. 1988) *J. Oral Path.* 17(4):145-191.
Jiang et al. "Copper-catalyzed coupling of amides and carbamates with vinyl halides" (2003) *Organic Letters* 5(20):3667-3669.
Kacinski et al. "Apoptosis and Cutaneous T Cell Lymphoma" (2001) *Annals of the New York Academy of Sciences* 941:194-199.
Kamens et al. "Identification and Characterization of ICH-2, a Novel Member of the Interleukin-1β-converting Enzyme Family of Cysteine Proteases" (Jun. 23, 1995) *J. Biol. Chem.* 270(25):15250-15256.
Kanegane et al. "Autoimmune Lymphoproliferative Syndrom Presenting with Glomerulonephritis" (2003) *Pediatr. Nephrol.* 18:454-456.
Karanewsky et al. "Conformationally Constrained Inhibitors of Caspase-1 (Interleukin-1β Converting Enzyme) and of the Human CED-3 Homologne Caspase-3) (CPP32, Apopain)" (1998) *Bioorg. Med. Chem. Lett.* 8:2757-2762.
Kimble et al. "Persistent Bone-Sparing Effect of Interleukin-1 Receptor Antagonist: A Hypothesis on the Role of IL-1 in Ovariectomy-Induced Bone Loss" (1994) *Laboratory Investigations* 55:260-265.
Knoblach et al. "Multiple Caspases are Activated after Traumatic Brain Injury: Evidence for Involvement in Functional Outcome" (2002) *J. Neurotrauma* 19(10):1155-1170.
Kostura et al. "Identification of a monocyte specific pre-interleukin 1 βconvertase activity" (Jul. 1989) *PNAS USA* 86(14):5227-5231.

(56) References Cited

OTHER PUBLICATIONS

Kozawa et al. "Synthesis of 3-alkoxycarbonyl-1β-methylcarbapenem using palladium-catalyzed amidation of vinyl halide (2002) *Tetrahedron Letters* 43(1):111-114.

Ku et al. "Interleukin-1β Converting Enzyme Inhibition Blocks Progression of Type II Collagen-Induced Arthritis in Mice" (May 1996) *Cytokine* 8(5):337-386.

Kuida et al. "Altered Cytokine Export and Apoptosis in Mice Deficient in Interleukin-1β Converting Enzyme" (Apr. 1995) *Science* 267(5206):2000-2003.

Layzer "Degenerative Diseases of the Nervous System" (1996) Cecil Textbook of Medicine, 20$^{th}$ Edition 2:2050-2057.

Lazebnik et al. "Cleavage of poly(ADP-ribose) polymerase by a proteinase with properties like ICE" (Sep. 22, 1994) *Nature* 371(6495):346-347.

Li "The Role of T Cell Apoptosis in Transplantation Tolerance" (2000)*Current Opinion in Immunology* 12(5):522-527.

Li et al. "Functional role of caspase-1 and caspase-3 in an ALS transgenic mouse model" (Apr. 14, 2000) *Science* 288(5464):335-339.

Lippke et al. "Identification and Characterization of CPP32/Mch2 Homolog 1, a Novel Cysteine Protease Similar to CPP32" (Jan. 26, 1996) *J. Biol. Chem.* 271(4):1825-1828.

Livingston "In Vitro and in Vivo Studies of ICE Inhibitors" (1997) *J. Cell. Biochem.* 64:19-26.

Lonnemann et al. "Differences in the Synthesis and Kinetics of release of interleukin 1α, interleukin 1β and tumor necrosis factor from human monouclear cells" (Sep. 1989) *Eur. J. Immunol.* 19(9):1531-1536.

MacKenzie et al. "An Inhibitor of the Interleukin-1β-Processing Enzyme Blocks IL-1 Release and Reduces Pyrexia and Acute Inflammation" (1994) Inflammation Research Association (7$^{th}$ Internat. Conf.), W42.

March et al. "Cloning, sequence and expression of two distinct human interleukin-1 complementary DNAs" (Jun. 20, 1985) *Nature* 315(6021):641-647.

Martin et al. "Protease activation during apoptosis: Death by a thousand cuts?" (Aug. 11, 1995) *Cell* 82(3):349-352.

Marx et al. "Cell death studies yield cancer clues" (Feb. 5, 1993) *Science* 259(5096):760-761.

Matteoli et al. "Asymmetric hydrogenation by an in situ prepared (S)-BINAP-RU(II) catalytic system" (1999) *J. Molecular Catalysis A: Chemical* 140:131-137.

McCarthy et al. "Inhibition of Interleukin-1 by an Interleukin-1 Receptor Antagonist Prevents Graft-Versus-Host Disease" (1991) *Blood* 78:1915-1918.

Miller et al. "Apoptosis" (Aug. 28, 1998) *Science* 281(5381):1301.

Miller et al. "Inhibition of Mature IL-1β Production in Murine Macrophages and a Murine Model of Inflammation by WIN 67694, an Inhibitor of IL-1β Converting Enzyme" (1995) *J. Immunol.* 154:1331-1338.

Miller et al. "The IL-1β Converting Enzyme as a Therapeutic Target" (Nov. 1993) *Ann. N.Y. Acad. Sci.* 696:133-148.

Miura et al. "Induction of Apoptosis in Fibroblasts by IL-1β-Converting Enzyme, a Mammalian Homolog of the C. elegans Cell Death Gene ced-3" (Nov. 19, 1993) *Cell* 75(4):653-660.

Mjalli et al. "Activated Ketones as Potent Reversible Inhibitors of Interleukin-1β Converting Enzyme" (1994) *Bioorg. Med. Chem. Lett.* 4(16):1965-1968.

Mjalli et al. "Phenylalkyl Ketones as Potent Reversible Inhibitors of Interleukin-1β Converting Enzyme" (1993) *Bioorg. Med. Chem. Lett.* 3(12):2689-2692.

Molineaux et al. "Interleukin 1β (IL-1β) processing in murine macrophages requires a structurally conserved homologue of human IL-1β converting enzyme" (Mar. 1, 1993) *PNAS USA* 90(5):1809-1813.

Mosely et al. "Determination of the minimum polypeptide lengths of the functionally active site of human interleukins 1α and 1β" (Jul. 1, 1987) *PNAS USA* 84(13):4572-4576.

Mullican et al. "The Synthesis and Evaluation of Peptidyl Aspartyl Aldehydes as Inhibitors of ICE" (1994) *Biorg. Med. Chem. Lett.* 4(19):2359-2364.

Mullin "Crystallization and Precipitation" (2002) Ullmann's Encyclopedia of Industrial Chemistry (published online Jan. 15, 2003 by Wiley-VCH Verlag GmbH & Cdo. K Ga A).

Munday et al. "Molecular Cloning and Pro-apoptotic Activity of ICE$_{rel}$II and ICE$_{rel}$III, Members of the ICE/CED-3 Family of Cysteine Proteases" (Jun. 30, 1995) *J. Biol. Chem.* 270(26):15870.

Muzio et al. "FLICE, a novel FADD-homologous ICE/CED-3-lik protease, is recruited to the CD95 (Fas/APO-1) Death-Inducing Signaling Complex" (Jun. 14, 1996) *Cell* 85(6):817-827 (abstract only).

Nagaraj et al. "Racemization at Proline Residues During Peptide Bond Formation: A Study of Diastereomeric Mixtures of Synthetic Alamethicin Fragments by 270 MHz $^1$H NMR" (1981) *Tetrahedron* 37:2001-2005.

Nagaraj et al. "Solution Phase Synthesis of Alamethicin I" (1981) *Tetrahedron* 37:1263-1270.

Nett-Fiordalisi et al. "Characterization and Activation of the Murine Interleukin-1β (IL-1β Converting Enzyme)" (1993) *J. Cell Biochem.* 53(Supp 17B):117.

Nicholson et al. "Identification and Inhibitaiton of the ICE/CED-3 Protease Necessary for Mammalian Apoptosis" (Jul. 6, 1995) *Nature* 376(6535):37-43.

Nicoletti et al. "Protection from experimental autoimmune diabetes in the non-obese diabetic mouse with soluble interleukin-i receptor" (1994) *Eur. J. Immunol.* 24:1843-1847.

Notice of Allowance and Fee(s) Due in U.S. Appl. No. 09/860,750 dated Apr. 7, 2008.

Notice of Allowance in U.S. Appl. No. 11/069,895 dated Sep. 4, 2009.

Notice of Allowance in U.S. Appl. No. 11/140,649 dated Dec. 31, 2008.

Office Action from U.S. Appl. No. 09/665,503 dated Apr. 2, 2002.
Office Action from U.S. Appl. No. 09/665,503 dated Dec. 14, 2001.
Office Action from U.S. Appl. No. 09/665,503 dated Jul. 2, 2001.
Office Action from U.S. Appl. No. 10/314,103 dated Apr. 2, 2007.
Office Action from U.S. Appl. No. 10/314,103 dated Apr. 7, 2004.
Office Action from U.S. Appl. No. 10/314,103 dated Dec. 29, 2004.
Office Action from U.S. Appl. No. 10/314,103 dated Jun. 28, 2006.
Office Action from U.S. Appl. No. 10/314,103 dated Oct. 5, 2005.
Office Action in U.S. Appl. No. 09/860,750 dated Apr. 26, 2005.
Office Action in U.S. Appl. No. 09/860,750 dated Aug. 10, 2004.
Office Action in U.S. Appl. No. 09/860,750 dated Dec. 15, 2003.
Office Action in U.S. Appl. No. 09/860,750 dated Jan. 6, 2006.
Office Action in U.S. Appl. No. 10/985,641 dated Jul. 26, 2007.
Office Action in U.S. Appl. No. 10/985,641 dated Jun. 26, 2008.
Office Action in U.S. Appl. No. 10/985,641 dated Mar. 26, 2008.
Office Action in U.S. Appl. No. 10/985,641 dated Oct. 14, 2008.
Office Action in U.S. Appl. No. 11/069,895 dated Apr. 1, 2008.
Office Action in U.S. Appl. No. 11/069,895 dated Dec. 24, 2008.
Office Action in U.S. Appl. No. 11/140,649 dated Jan. 25, 2007.
Office Action in U.S. Appl. No. 11/140,649 dated Sep. 24, 2007.

Okamoto et al. "Peptide Based Interleukin-1β Converting Enzyme (ICE) Inhibitors: Synthesis, Structure Activity Relationships and Crystallographic Study of the ICE-inhibitor Complex" (Jan. 1999) *Chem. Pharm. Bull.* 47(1):11-21.

Okamura et al. "A Novel Costimulatory Factor for Gamma Interferon Induction Found in the Livers of Mice Causes Endotoxic Shock" (Oct. 1995) *Infection and Immunity* 63(10):3966-3972.

Okamura et al. "Cloning of new cytokine that induces IFN-γ production by T cells" (Nov. 2, 1995) *Nature* 378(6552):88-91.

Ona et al. "Inhibition of caspase-1 slows disease progression in a mouse model of Huntington's disease" (May 20, 1999) *Nature* 399(6733):263-267.

Oppenheim et al. "There is more than one interleukin 1" (Feb. 1986) *Immunology Today* 7(2):45-56.

Paszkowski et al. "Therapeutic Application of Caspase 1/Interleukin-1β-Converting Enzyme Inhibitor Decreases the Death Rate in Severe Acute Experimental Pancreatitis" (2002) *Annals of Surgery* 235(1):68-76.

(56) References Cited

OTHER PUBLICATIONS

Pennington et al. "Synthesis of a Fluorogenic Interleukin-1β Converting Enzyme Substrate Based on Resonance Energy Transfer" (1994) *Pept. Res.* 7:72-76.
Pettipher et al. "Interleukin 1 induces leukocyte infiltration and cartilage proteoglycan degradation in the synovial joint" (Nov. 1986) *PNAS USA* 83(22):8749-8753.
Plattner et al. "Obstacles to drug development from peptide leads" (1990 ed.) in Drug Discovery Technologies (Ellis Horwood, Chichester, England) pp. 92-126.
Pomerantz et al. "Inhibition of caspase 1 reduces human myocardial ischemic dysfunction via inhibition of IL-18 and IL-1β" (2001) *PNAS USA* 98(5):2871-2876.
Prasad et al. "$P_1$ Aspartate-Based α-Arylacyloxy- and α-Aryloxymethyl Ketones as Potent Time-Dependent Inhibitors of Interleukin 1β Converting Enzyme" (Jun. 21-25, 1994) *Am. Chem. Soc. Abs.* ($24^{th}$ Med. Chem. Symp.) 66.
Rau et al. "Differential Effects of Caspase-1/Interleukin-1β-Converting Enzyme on Acinar Cell Necrosis and Apoptosis in Severe Acute Experimental Pancreatitis" (Jul. 2001) *Laboratory Investigation* 81(7): 1001-1013.
Ravizza et al. Abstract Inactivation of caspase-1 in rodent brain: a novel anticonvulsive strategy (Jul. 2006) *Epilepsia.* 47(7): 1160-1168.
Ray et al. "Viral Inhibition of Inflammation: Cowpox Virus Encodes an Inhibitor of the Interleukin-1β Converting Enzyme" (May 15, 1992) *Cell* 69:597-604.
Reiter "Peptidic p-Nitroanilide Substrates of Interleukin-1β-Converting Enzyme" (1994) *Int. J. Pept. Protein Res.* 43:87-96.
Revesz et al. "Synthesis of P1 Aspartate-Based Peptide Acyloxymethyl and Fluoromethyl Ketones as Inhibitors of Interleukin-1β-Converting Enzyme" (1994) *Tetrahedron Lett.* 35(52):9693-9696.
Robinson et al. "Synthesis of a Peptidyl Difluoro Ketone Bearing the Aspartic Acid Side Chain: An Inhibitor of Interleukin-1β Converting Enzyme" (1992) *J. Org. Chem.* 57:7309-7314.
Rouquet et al. "ICE inhibitor YVADcmk is a potent therapeutic agent against in vivo liver apoptosis" (1996) *Current Biology* 6(9):1192-1195.
Saburi et al. "Asymmetric Transfer Hydrogenation of Prochiral Carboxylic Acids Catalyzed by a Five-Coordinate Ru(II)-binap Complex" (1992) *Tetrahedron Lett.* 33(39):5783-5786.
Schierle et al. "Caspase Inhibition Reduces Apoptosis and Increases Survival of Nigral Transplants" (Jan. 1999) *Nature Medicine* 15(1):97-100.
Schindler et al. "Transcriptional Responses to Polypeptide Ligands: the JAK-STAT" (Jun. 1995) *Ann. Rev. Biochem.* 64:621-652.
Schmidt et al. "Synthesis and Evaluation of Aspartyl .alpha.-Chloro-, α-Aryloxy-, and α-Arylacyloxymethyl Ketones as Inhibitors of Interleukin-1β Converting Enzyme" (1994) Am. Chem. Soc. Abs. ($208^{th}$ Natl. Mtg.) MEDI 4.
Siegmund "Interleukin-1β converting enzyme (caspase-1) in intestinal inflammation" (2002) *Biochem. Pharmacol.* 65:1-8.
Simone "Oncology Introduction" (1996) Cecil Textbook of Medicine, $20^{th}$ Edition 1:1004-1010.
Sleath et al. "Substrate Specificity of the Protease that Processes Human Interleukin-1β" (Aug. 25, 1990) *J. Biol. Chem.* 265(24):14526-14528.
Spatola "Chapter 5. Peptide Backbone Modifications: A Structure-Activity Analysis of Peptides Containing Amide Bond Surrogates, Conformational Constrates and Related . . . " (1983) *Chem. and Biochem. of Amino Acids, Peptides, and Proteins* (Weinstein, B., ed., Marcel Dekker, Inc., New York) 7(5):267-357.
Stack et al. "IL-converting enzyme/caspase-1 inhibitor VX-765 blocks the hypersensitive response to an inflammatory stimulus in monocytes from familial cold autoinflammatory syndrome patients" (Aug. 15, 2005) *J. Immunol.* 175(4):2630-2634.
Steller "Mechanisms and Genes of Cellular Suicide" (Mar. 10, 1995) *Science* 267(5203):1445-1449.
Strasser "The Role of Bim, a Proapoptotic BH3-Only Member of the Bc1-2 Family, in Cell-Death Control" (2000) *Annals of the New York Academy of Sciences* 917:541-548.
Taniguchi "Regulation of the interferon system and cell growth by the IRF transcription factors" (Sep. 1995) *J. Cancer Res. Clin. Oncol.* 121(9):516-520.
Tartour et al. "Analysis of interleukin 6 gene expression in cervical neoplasia using a quantitative polymerase chain reaction assay: evidence for enhanced interleukin 6 gene expression in invasive carcinoma" (Dec. 1, 1994) *Cancer Res.* 54(23):6243-6248.
Thakur et al. "Caspase-1 Inhibitor Reduces Severity of Pseudomones aeruginosa Keratitis in Mice" (Sep. 2004) *Invest Ophthalmol Vis Sci.* 45:3177-3184.
Thornberry "Caspases: Key Mediators of Apoptosis" (May 1998) *Chem. Biol.* 5:R97-R103.
Thornberry et al. "A novel heterodimeric cysteine protease is required for interleukin-1β processing in monocytes" (Apr. 30, 1992) *Nature* 356(6372):768-774.
Thornberry et al. "Inactivation of Interleukin-1β Converting Enzyme by Peptide (Acycloxy)methyl Ketones" (1994) *Biochemistry* 33:3934-3940.
Tocci "Structure and Function of Interleukin-1 beta converting enzyme" (1997) *Vitam. Horm.* (Vitam. Horm. 53:27-63.
Tsuchiyama "Efficacy of Galectins in the Amelioration of Nephrotoxic Serum Nephritis in Wistar Kyoto Rats" (2000) *Kidney International* 58(5):1941-1952.
Uhl et al. "Secretion of Human Monocyte Mature IL-1β: Optimization of Culture Conditions and Inhibition by ICE Inhibitors" (1995) *Inflammation Res.* 44(Supp. 2):S211-S212.
Ushio et al. "Cloning of the cDNA for human IFN-gamma-inducing factor, expression in *Escherichia coli*, and studies on the biologic activities of the protein" (Jun. 1, 1996) *J. Immunol.* 156:4274-4279.
Van De Craen et al. "Characterization of Seven Murine Caspase Family Members" (Feb. 10, 1997) *FEBS Lett.* 403(1):61-69.
Van Den Brande "Treating Crohn's Disease by Inducing T Lymphocyte Apoptosis" (2002) *Annals of the New York Academy of Sciences* 973:166-180.
Veale et al. "Orally Active Trifluoromethyl Ketone Inhibitors of Human Leukocyte Elastase" (1997) *J. Med. Chem.* 40:3173-3181.
Vidal-Vanaclocha "Interleukin-1 Receptor Blockade Reduces the Number and Size of Murine B16 Melanoma Hepatic Metastases" (May 15, 1994) *Cancer Res.* 54(10):2667-2672.
Villa et al. "Caspases and Caspase Inhibitors" (Oct. 1997) *Trends in Biochemical Sciences* 22(10):388-393.
Vincenz et al. "Fas-associated Death Domain Protein Interleukin-1β-converting Enzyme 2 (FLICE2), an ICE/Ced-3 Homologue, is Proximally Involved in CD95- and p55-mediated Death Signaling" (Mar. 7, 1997) *J. Biol. Chem.* 272(10):6578-6583.
Wallace et al. "Palladium-catalyzed amidation of enol triflates: a new synthesis of enamides" (2003) *Organic Letters* 5(24):4749-4752.
Wang et al. "Ich-1, an ICE/CED-3-related gene, encodes both positive and negative regulators of programmed cell death" (Sep. 9, 1994) *Cell* 78(5):739-750.
Wang et al. "Identification and Characterization of Ich-3, a Member of the Interleukin-1β Converting Enzyme (ICE)/Ced-3 Family and an Upstream Regulator of ICE" (Aug. 23, 1996) *J. Biol. Chem.* 271(34):20580-20587.
Wannamaker et al. "(S)-1-((S)-2- {[1 -(4-Amino-3.cndot.chlorophenyl)-methanoyl]-amino)-3,3-d.imethyl-butanoyl)-pyrrolidine-2-carboxylic ax id ((2R,3S)-2-ethoxy-5-oxo-tetrahydro-furan-3-yl)-amide (VX-765), an Orally Available Selective Interleukin (IL)-Converting Enzyme/Caspase-1 Inhibitor, Exhibits Potent Anti-Inflammatory Activities by Inhibiting the Release of IL-1β and IL-18" (2007) *JPET* 321(2):509-516.
Weinstein "Chemistry and Biochemistry of Amino Acids, Peptides and Proteins, Passage" (1983) Chem. Biochem. Amino Acids, Pept., Prot. 7:266-357.
Wetzler et al. "Altered Levels of Interleukin-1β and Interleukin-1 Receptor Antagonist in Chronic Myelogenous Leukemia: Clinical and Prognostic Correlates" (Nov. 1, 1994) *Blood* 84(9):3142-3147.
Whyte et al. "The last cut is the deepest" (Jul. 6, 1995) *Nature* 376(6535):17-18.

(56) References Cited

OTHER PUBLICATIONS

Wilson et al. "Structure and mechanism of interleukin-1β converting enzyme" (Jul. 28, 1994) *Nature* 370(6487):270-275.
Witek et al. "Pan-Caspase Inhibitor VX-166 Reduces Fibrosis in an Animal Model of Nonalcoholic Steatohepatitis" (Nov. 2009) *Hepatology* 50(5):1421-1430.
Wood et al. "Isolation of an interleukin-1-like factor from human joint effusions" (Aug. 1983) *Arthritis Rheum.* 26(8):975-983.
Yakovlev et al. "Activation of CPP32-Like Caspases Contributes to Neuronal Apoptosis and Neurological Dysfunction after Traumatic Brain Injury" (Oct. 1, 1997) *J. Neuroscience* 17(19):7415-7424.
Yaoita et al. "Attenuation of Ischemia/Reperfusion Injury in Rats by a Caspase Inhibitor" (1998) *Circulation* 97(3):276-281.
Yuan "Molecular Control of Life and Death" (1995) *J. Curr. Opin. Cell Biol.* 7(2):211-214.
Yuan et al. "The C. elegans cell death gene ced-3 encodes a protein similar to mammalian interleukin-1β-converting enzyme" (Nov. 19, 1993) *Cell* 75(4):641-652.
Zhu et al. "Highly Efficient Asymmetric Synthesis of β-Amino Acid Derivatives Via Rhodium-Catalyzed Hydrogenation of β-(Acylamino)acrylates" (1999) *J. Org. Chem.* 64:6907-6910.

PRODRUG OF AN ICE INHIBITOR

This is a continuation of U.S. application Ser. No. 14/747,578, filed Jun. 23, 2015, issued as U.S. Pat. No. 9,487,555, which is a continuation of U.S. application Ser. No. 13/709,610, filed Dec. 10, 2012, issued as U.S. Pat. No. 9,156,880, which is a divisional of U.S. application Ser. No. 13/210,712, filed Aug. 16, 2011, issued as U.S. Pat. No. 8,329,662, which is a divisional of U.S. application Ser. No. 12/165,838, filed Jul. 1, 2008, issued as U.S. Pat. No. 8,022,041, which is a divisional of U.S. application Ser. No. 09/860,750, filed May. 18, 2001, issued as U.S. Pat. No. 7,417,029, which claims benefit of U.S. Provisional Application Ser. No. 60/205,439, filed May. 19, 2000.

TECHNICAL FIELD OF THE INVENTION

The present invention relates to a novel interleukin-1β converting enzyme (ICE) inhibitor in its prodrug form. The compound and pharmaceutical compositions thereof are useful as agents to treat interleukin-1-(IL-1), apoptosis-, interferon-γ inducing factor-(IL-18), or interferon-γ (IFN-γ) mediated diseases, including inflammatory diseases, autoimmune diseases, destructive bone disorders, proliferative disorders, infectious diseases, and degenerative diseases. This invention also relates to methods for inhibiting ICE activity and decreasing IL-18 production and IFN-γ production and methods for treating interleukin-1, apoptosis-, and interferon-γ-mediated diseases using the compositions of this invention.

BACKGROUND OF THE INVENTION

Interleukin-1 (IL-1) is a major pro-inflammatory and immunoregulatory protein that stimulates fibroblast differentiation and proliferation, the production of prostaglandins, collagenase and phospholipase by synovial cells and chondrocytes, basophil and eosinophil degranulation and neutrophil activation. Oppenheim, J. H. et al, *Immunology Today,* 7, pp. 45-56 (1986). As such, it is involved in the pathogenesis of chronic and acute inflammatory and autoimmune diseases. For example, in rheumatoid arthritis, IL-1 is both a mediator of inflammatory symptoms and of the destruction of the cartilage proteoglycan in afflicted joints. Wood, D. D. et al., *Arthritis Rheum.* 26, 975, (1983); Pettipher, E. J. et al., *Proc. Natl. Acad. Sci. USA* 71, 295 (1986); Arend, W. P. and Dayer, J. M., *Arthritis Rheum.* 38, 151 (1995). IL-1 is also a highly potent bone resorption agent. Jandiski, J. J., *J. Oral Path* 17, 145 (1988); Dewhirst, F. E. et al., *J. Immunol.* 8, 2562 1985). It is alternately referred to as "osteoclast activating factor" in destructive bone diseases such as osteoarthritis and multiple myeloma. Bataille, R. et al., *Int. J. Clin. Lab. Res.* 21(4), 283 (1992). In certain proliferative disorders, such as acute myelogenous leukemia and multiple myeloma, IL-1 can promote tumor cell growth and adhesion. Bani, M. R., *J. Natl. Cancer Inst.* 83, 123 (1991); Vidal-Vanaclocha, F., *Cancer Res.* 54, 2667 (1994). In these disorders, IL-1 also stimulates production of other cytokines such as IL-6, which can modulate tumor development (Tartour et al., *Cancer Res.* 54, p. 6243 (1994). IL-1 is predominantly produced by peripheral blood monocytes as part of the inflammatory response and exists in two distinct agonist forms, IL-1α and IL-1β. Mosely, B. S. et al., *Proc. Nat. Acad. Sci.,* 84, pp. 4572-4576 (1987); Lonnemann, G. et al., *Eur. J. Immunol.,* 19, pp. 1531-1536 (1989).

IL-1β is synthesized as a biologically inactive precursor, pro-IL-1β. Pro-IL-1β lacks a conventional leader sequence and is not processed by a signal peptidase. March, C. J., *Nature,* 315, pp. 641-647 (1985). Instead, pro-IL-1β is cleaved by interleukin-1β converting enzyme (ICE) between Asp-116 and Ala-117 to produce the biologically active C-terminal fragment found in human serum and synovial fluid. Sleath, P. R., et al., *J. Biol. Chem.,* 265, pp. 14526-14528 (1992); A. D. Howard et al., *J. Immunol.,* 147, pp. 2964-2969 (1991). ICE is a cysteine protease localized primarily in monocytes. It converts precursor IL-1β to the mature form. Black, R. A. et al., *FEBS Lett.,* 247, pp. 386-390 (1989); Kostura, M. J. et al., *Proc. Natl. Acad. Sci. U.S.A.,* 86, pp. 5227-5231 (1989). Processing by ICE is also necessary for the transport of mature IL-1β2 through the cell membrane.

ICE (or caspase-1) is a member of a family of homologous enzymes called caspases. These homologs have sequence similarities in the active site regions of the enzymes. Such homologs (caspases) include TX (or $ICE_{rel-II}$ or ICH-2) (caspase-4) (Faucheu, et al., *EMBO J.,* 14, p. 1914 (1995); Kamens J., et al., *J. Biol. Chem.,* 270, p. 15250 (1995); Nicholson et al., *J. Biol. Chem.,* 270 15870 (1995)), TY (or $ICE_{rel-III}$) (caspase-5) (Nicholson et al., *J. Biol. Chem.,* 270, p. 15870 (1995); ICH-1 (or Nedd-2) (caspase-2) (Wang, L. et al., *Cell,* 78, p. 739 (1994)), MCH-2 (caspase-6), (Fernandes-Alnemri, T. et al., *Cancer Res.,* 55, p. 2737 (1995), CPP32 (or YAMA or apopain) (caspase-3) (Fernandes-Alnemri, T. et al., *J. Biol. Chem.,* 269, p. 30761 (1994); Nicholson, D. W. et al., *Nature,* 376, p. 37 (1995)), CMH-1 (or MCH-3) (caspase-7) (Lippke, et al., *J. Biol. Chem.,* 271(4), p1825-1828 (1996)); Fernandes-Alnemri, T. et al., *Cancer Res.,* (1995)), Mch5 (caspase-8) (Muzio, M. et. al., *Cell* 85(6), 817-827, (1996)), MCH-6 (caspase-9) (Duan, H. et. al., *J. Biol. Chem.,* 271(34), p. 16720-16724 (1996)), Mch4 (caspase-10) (Vincenz, C. et. al., *J. Biol. Chem.,* 272, p. 6578-6583 (1997); Fernandes-Alnemri, T. et. al., *Proc. Natl. Acad. Sci.* 93, p. 7464-7469 (1996)), Ich-3 (caspase-11) (Wang, S. et. al., *J. Biol. Chem.,* 271, p. 20580-20587 (1996)), mCASP-12 (caspase-12), (Van de Craen, M. et. al., *FEBS Lett.* 403, p. 61-69 (1997); Yuan, Y. and Miura, M. PCT Publication WO95/00160 (1995)), ERICE (caspase-13), (Humke, E. W., et. al., *J. Biol. Chem.,* 273(25) p. 15702-15707 (1998)), and MICE (caspase-14) (Hu, S. et. al., *J. Biol. Chem.,* 273(45) p. 29648-29653 (1998)).

Each of these ICE homologs, as well as ICE itself, is capable of inducing apoptosis when overexpressed in transfected cell lines. Inhibition of one or more of these homologs with the peptidyl ICE inhibitor Tyr-Val-Ala-Asp-chloromethylketone results in inhibition of apoptosis in primary cells or cell lines. Lazebnik et al., *Nature,* 371, p. 346 (1994).

Caspases also appear to be involved in the regulation of programmed cell death or apoptosis. Yuan, J. et al., *Cell,* 75, pp. 641-652 (1993); Miura, M. et al., *Cell,* 75, pp. 653-660 (1993); Nett-Fiordalisi, M. A. et al., *J. Cell Biochem.,* 17B, p. 117 (1993). In particular, ICE or ICE homologs are thought to be associated with the regulation of apoptosis in neurodegenerative diseases, such as Alzheimer's and Parkinson's disease. Marx, J. and M. Baringa, *Science,* 259, pp. 760-762 (1993); Gagliardini, V. et al., *Science,* 263, pp. 826-828 (1994). Inhibition of caspases have also recently been shown to be effective in a murine model of amylotropic lateral sclerosis. Li, M. et al.; *Science,* 288, pp. 335-339 (2000). Therapeutic applications for inhibition of apoptosis may include, among others, treatment of Alzheimer's disease, Parkinson's disease, stroke, myocardial infarction, spinal atrophy, and aging.

ICE has been demonstrated to mediate apoptosis (programmed cell death) in certain tissue types. Steller, H., *Science*, 267, p. 1445 (1995); Whyte, M. and Evan, G., *Nature*, 376, p. 17 (1995); Martin, S. J. and Green, D. R., *Cell*, 82, p. 349 (1995); Alnemri, E. S., et al., *J. Biol. Chem.*, 270, p. 4312 (1995); Yuan, J. *Curr. Opin. Cell Biol.*, 7, p. 211 (1995). A transgenic mouse with a disruption of the ICE gene is deficient in Fas-mediated apoptosis (Kuida, K. et al., *Science* 267, 2000 (1995)). This activity of ICE is distinct from its role as the processing enzyme for pro-IL-1β. It is conceivable that in certain tissue types, inhibition of ICE may not affect secretion of mature IL-1β, but may inhibit apoptosis.

Enzymatically active ICE has been previously described as a heterodimer composed of two subunits, p20 and p10 (20 kDa and 10 kDa molecular weight, respectively). These subunits are derived from a 45 kDa proenzyme (p45) by way of a p30 form, through an activation mechanism that is autocatalytic. Thornberry, N. A. et al., *Nature*, 356, pp. 768-774 (1992). The ICE proenzyme has been divided into several functional domains: a prodomain (p14), a p22/20 subunit, a polypeptide linker and a p10 subunit. Thornberry et al., supra; Casano et al., *Genomics*, 20, pp. 474-481 (1994).

Full length p45 has been characterized by its cDNA and amino acid sequences. PCT patent applications WO 91/15577 and WO 94/00154. The p20 and p10 cDNA and amino acid sequences are also known. Thornberry et al., supra. Murine and rat ICE have also been sequenced and cloned. They have high amino acid and nucleic acid sequence homology to human ICE. Miller, D. K. et al., *Ann. N.Y. Acad. Sci.*, 696, pp. 133-148 (1993); Molineaux, S. M. et al., *Proc. Nat. Acad. Sci.*, 90, pp. 1809-1813 (1993). The three-dimensional structure of ICE has been determined at atomic resolution by X-ray crystallography. Wilson, K. P., et al., *Nature*, 370, pp. 270-275 (1994). The active enzyme exists as a tetramer of two p20 and two p10 subunits.

Recently, ICE and other members of the ICE/CED-3 family have been linked to the conversion of pro-IL-18 to IL-18 or to the production of IFN-γ in vivo (PCT application PCT/US96/20843, publication no. WO 97/22619, which is incorporated herein by reference). IL-18 is synthesized in vivo as the precursor protein "pro-IL-18".

Interleukin-18 (IL-18), formerly interferon-gamma inducing factor, (IGIF) is an approximately 18-kDa polypeptide that stimulates T-cell production of interferon-gamma (IFN-γ-). IL-18 is produced by activated Kupffer cells and macrophages in vivo and is exported out of such cells upon endotoxin stimulation. Like IL-1β, IL-18 is synthesized as a biologically inactive precursor molecule lacking a single peptide, which requires cleavage into an active, mature molecule by IL-1β converting enzyme. Dinerello, C. A. *Methods*, 19, pp 121-132 (1999). Thus, a compound that decreases IL-18 production would be useful as an inhibitor of such T-cell stimulation which in turn would reduce the levels of IFN-γ production by those cells.

IFN-γ is a cytokine with immunomodulatory effects on a variety of immune cells. In particular, IFN-γ is involved in macrophage activation and Th1 cell selection (F. Belardelli, *APMIS*, 103, p. 161 (1995)). IFN-γ exerts its effects in part by modulating the expression of genes through the STAT and IRF pathways (C. Schindler and J. E. Darnell, *Ann. Rev. Biochem.*, 64, p. 621 (1995); T. Taniguchi, *J. Cancer Res. Clin. Oncol.*, 121, p. 516 (1995)).

Mice lacking IFN-γ or its receptor have multiple defects in immune cell function and are resistant to endotoxic shock (S. Huang et al., *Science*, 259, p. 1742 (1993); D. Dalton et al., *Science*, 259, p. 1739 (1993); B. D. Car et al., *J. Exp. Med.*, 179, p. 1437 (1994)). Along with IL-12, IL-18 appears to be a potent inducer of IFN-γ production by T cells (H. Okamura et al., *Infection and Immunity*, 63, p. 3966 (1995); H. Okamura et al., *Nature*, 378, p. 88 (1995); S. Ushio et al., *J. Immunol.*, 156, p. 4274 (1996)).

IFN-γ has been shown to contribute to the pathology associated with a variety of inflammatory, infectious and autoimmune disorders and diseases. Thus, compounds capable of decreasing IFN-γ production would be useful to ameliorate the effects of IFN-γ related pathologies.

Accordingly, compositions and methods capable of regulating the conversion of pro-IL-18 to IL-18 would be useful for decreasing IL-18 and IFN-γ production in vivo, and thus for ameliorating the detrimental effects of these proteins which contribute to human disorders and diseases.

Caspase inhibitors represent a class of compounds useful for the control of inflammation or apoptosis or both. Peptide and peptidyl inhibitors of ICE have been described (PCT patent applications WO 91/15577, WO 93/05071, WO 93/09135, WO 93/12076, WO 93/14777, WO 93/16710, WO 95/35308, WO 96/30395, WO 96/33209 and WO 98/01133; European patent applications 503 561, 547 699, 618 223, 623 592, and 623 606; and U.S. Pat. Nos. 5,434, 248, 5,710,153, 5,716,929, and 5,744,451). Such peptidyl inhibitors of ICE have been observed to block the production of mature IL-1β in a mouse model of inflammation (vide infra) and to suppress growth of leukemia cells in vitro (Estrov et al., *Blood*, 84, 380a (1994)). However, due to their peptidic nature, such inhibitors are typically characterized by undesirable pharmacologic properties, such as poor cellular penetration and cellular activity, poor oral absorption, instability and rapid metabolism. Plattner, J. J. and D. W. Norbeck, in *Drug Discovery Technologies*, C. R. Clark and W. H. Moos, Eds. (Ellis Horwood, Chichester, England, 1990), pp. 92-126. These properties have hampered their development into effective drugs.

Non-peptidyl compounds have also been reported to inhibit ICE in vitro. PCT patent application WO 95/26958; U.S. Pat. No. 5,552,400; Dolle et al., *J. Med. Chem.*, 39, pp. 2438-2440 (1996). It is not clear however whether these compounds have the appropriate pharmacological profiles to be therapeutically useful.

WO 99/47545 describes a novel class of caspase inhibitors reported to have a favorable in vivo profile. These inhibitors are represented by the formula:

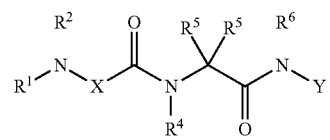

where X, Y, and $R^1$-$R^6$ are various substituents. Among the many examples of this class of inhibitors, the following structure was disclosed:

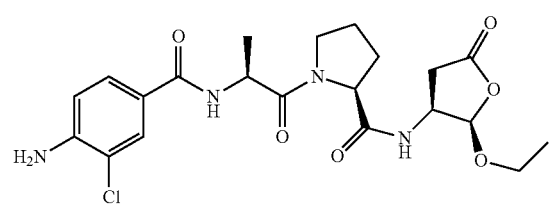

98d

As is known in the art, the bioavailability of compounds within a structural class is difficult to predict. Relatively minor structural modifications often have a large impact on the absorption of a compound, its blood level concentrations and/or its half-life. For example, such variations in bioavailability can be seen from the data in WO 99/47545. As a consequence, structurally related compounds that have very good in vitro potency may vary in therapeutic effectiveness.

Though progress has been made in improving the bioavailability of ICE inhibitors, there continues to be a need to identify and develop compounds that can effectively inhibit caspases, and that have improved in vivo activity. Such compounds would be useful as agents for preventing and treating chronic and acute forms of IL-1-, apoptosis-, IL-18-, or IFN-γ-mediated diseases, as well as inflammatory, autoimmune, destructive bone, proliferative, infectious, or degenerative diseases.

DESCRIPTION OF THE INVENTION

This invention provides a novel ICE inhibitor prodrug compound with surprisingly good bioavailability in mammals. The compound is represented by formula I:

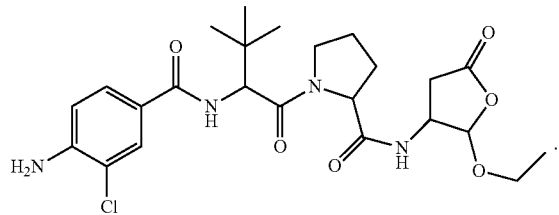

I

Compound I may be used alone or in combination with other therapeutic or prophylactic agents, such as antibiotics, immunomodulators or other anti-inflammatory agents, for the treatment or prevention of diseases mediated by IL-1, apoptosis, IL-18, or IFN-γ. This invention also relates to pharmaceutically acceptable derivatives and prodrugs of the compound.

Compound I itself is a prodrug that undergoes bioconversion to an active ICE inhibitor II:

I ⟶

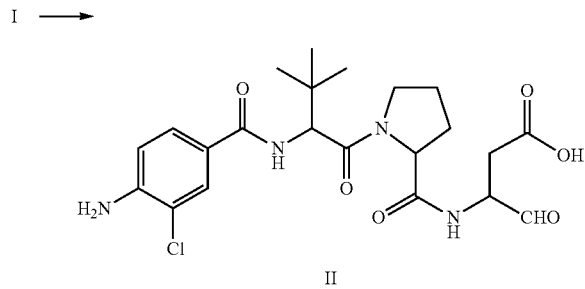

II

Compound I has better in vivo activity upon oral and/or intravenous administration than the parent or active form of the drug. The active form, aspartic aldehyde II, exhibits less than optimal in vivo activity, primarily because of poor bioavailability, and is therefore not well-suited for direct therapeutic use. Generally, poor bioavailability may result for any of the following reasons: the active form is not stable in the animal gut following ingestion, is not well-absorbed through the gut and/or is not well-delivered to the biological compartment (e.g., the brain or lymphatic system) for which it is intended. While the prodrug I shows enhanced bioavailability relative to its active form II, this invention is not limited to any particular mechanism by which the bioavailability is enhanced.

Applicants studied a number of prodrug ICE inhibitors, including examples listed in the aforementioned WO 99/47545. Bioavailability was determined by quantitating the amount of ICE inhibitor in rat plasma after oral administration, as described below. Compound I was found to have unexpectedly improved bioavailability relative to other prodrug ICE inhibitors tested, including some that were closely related in structure.

The structure for compound I depicted herein is meant to include all stereochemical forms of the compound; i.e., the R and S configurations for each asymmetric center. Therefore, single stereochemical isomers as well as enantiomeric and diastereomeric mixtures of the present compound are within the scope of the invention. A preferred isomer is compound I-A which has the "S" configuration at the carbon bearing the tert-butyl group, has the "S" configuration at the 2-position of the proline ring, has the "S" configuration at the 3-position of the furanone ring, and has the "R" configuration at the 2-ethoxy position of the furanone ring, as shown below:

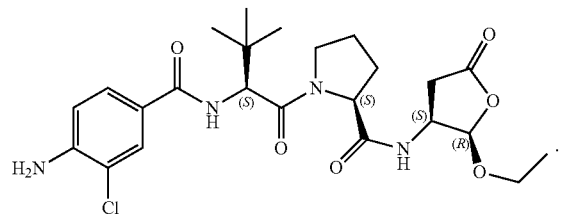

I-A

Another preferred isomer is compound I-B:

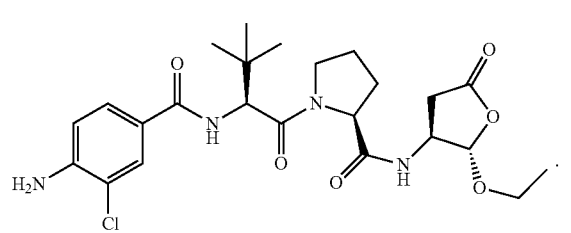

I-B

Unless otherwise stated, structures depicted herein are also meant to include compounds which differ only in the presence of one or more isotopically enriched atoms. For example, compounds having the present structures except for the replacement of a hydrogen by a deuterium or tritium, or the replacement of a carbon by a $^{13}C$— or $^{14}C$-enriched carbon are within the scope of this invention.

The compounds of this invention may be prepared in general by methods known to those skilled in the art for analogous compounds, as illustrated by the general scheme below and by the preparative examples below

Synthetic Scheme for Compound I-A

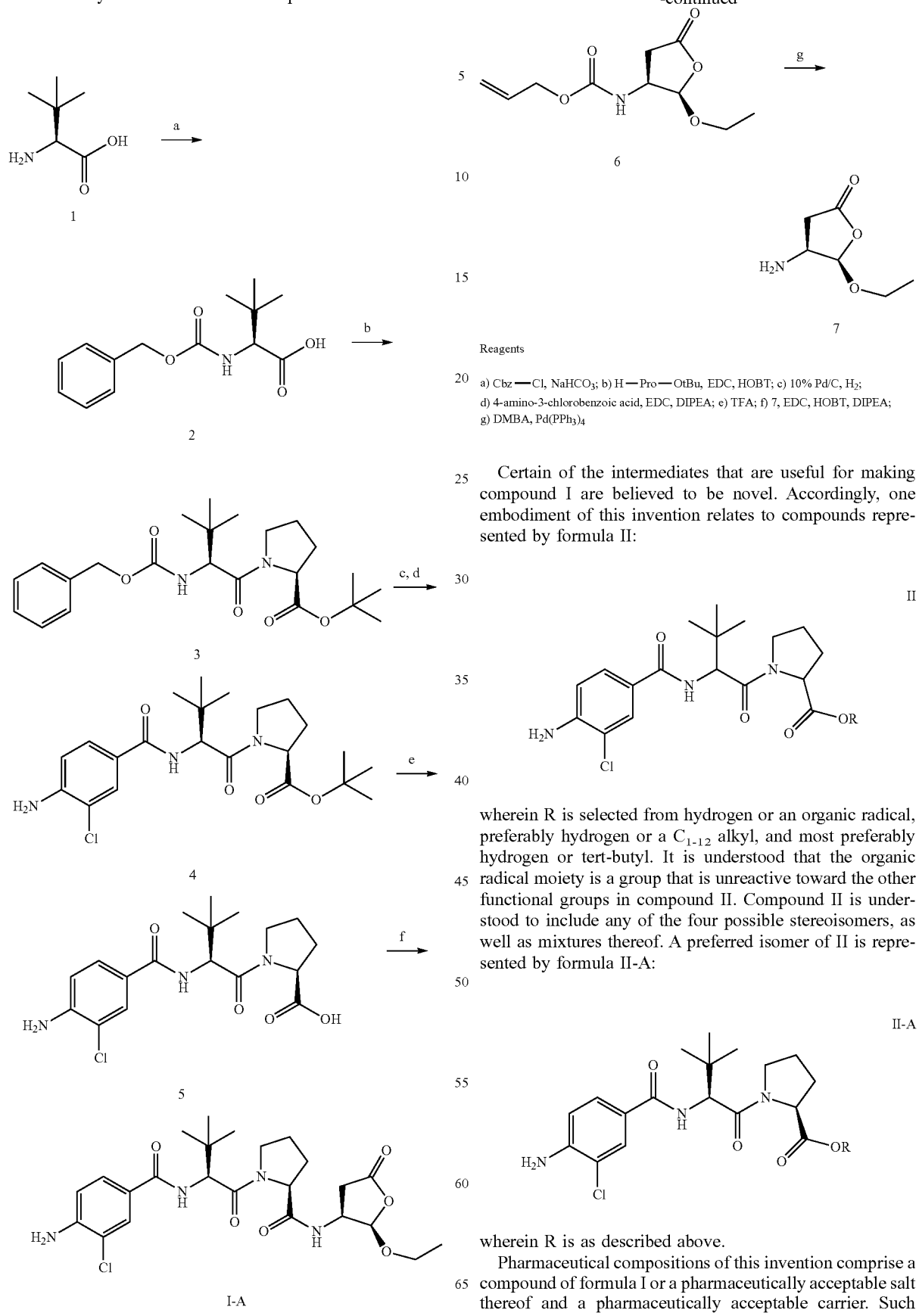

Reagents a) Cbz—Cl, NaHCO$_3$; b) H—Pro—OtBu, EDC, HOBT; c) 10% Pd/C, H$_2$;
d) 4-amino-3-chlorobenzoic acid, EDC, DIPEA; e) TFA; f) 7, EDC, HOBT, DIPEA;
g) DMBA, Pd(PPh$_3$)$_4$ Certain of the intermediates that are useful for making compound I are believed to be novel. Accordingly, one embodiment of this invention relates to compounds represented by formula II:

II wherein R is selected from hydrogen or an organic radical, preferably hydrogen or a C$_{1-12}$ alkyl, and most preferably hydrogen or tert-butyl. It is understood that the organic radical moiety is a group that is unreactive toward the other functional groups in compound II. Compound II is understood to include any of the four possible stereoisomers, as well as mixtures thereof. A preferred isomer of II is represented by formula II-A:

II-A wherein R is as described above.

Pharmaceutical compositions of this invention comprise a compound of formula I or a pharmaceutically acceptable salt thereof and a pharmaceutically acceptable carrier. Such compositions may optionally comprise an additional therapeutic agent. Such agents include, but are not limited to, an anti-inflammatory agent, a matrix metalloprotease inhibitor, a lipoxygenase inhibitor, a cytokine antagonist, an immunosuppressant, an anti-cancer agent, an anti-viral agent, a cytokine, a growth factor, an immunomodulator, a prostaglandin or an anti-vascular hyperproliferation compound.

The term "pharmaceutically acceptable carrier" refers to a non-toxic carrier that may be administered to a patient, together with a compound of this invention, and which does not destroy the pharmacological activity thereof.

Pharmaceutically acceptable carriers that may be used in the pharmaceutical compositions of this invention include, but are not limited to, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, wool fat and self-emulsifying drug delivery systems (SEDDS) such as α-tocopherol, polyethyleneglycol 1000 succinate, or other similar polymeric delivery matrices.

In pharmaceutical composition comprising only a compound of formula I as the active component, methods for administering these compositions may additionally comprise the step of administering to the subject an additional agent. Such agents include, but are not limited to, an anti-inflammatory agent, a matrix metalloprotease inhibitor, a lipoxygenase inhibitor, a cytokine antagonist, an immunosuppressant, an anti-cancer agent, an anti-viral agent, a cytokine, a growth factor, an immunomodulator, a prostaglandin or an anti-vascular hyperproliferation compound.

The term "pharmaceutically effective amount" refers to an amount effective in treating or ameliorating an IL-1-, apoptosis-, IL-18-, or IFN-γ-mediated disease in a patient. The term "prophylactically effective amount" refers to an amount effective in preventing or substantially lessening IL-1-, apoptosis-, IL-18-, or IFN-γ-mediated diseases in a patient.

The compounds of this invention may be employed in a conventional manner for controlling IL-18 and IFN-γ levels in vivo and for treating diseases or reducing the advancement or severity of effects which are mediated by IL-1, apoptosis, IL-18, or IFN-γ. Such methods of treatment, their dosage levels and requirements may be selected by those of ordinary skill in the art from available methods and techniques.

For example, a compound of this invention may be combined with a pharmaceutically acceptable adjuvant for administration to a patient suffering from an IL-1-, apoptosis-, IL-18-, or IFN-γ-mediated disease in a pharmaceutically acceptable manner and in an amount effective to lessen the severity of that disease.

Alternatively, the compounds of this invention may be used in compositions and methods for treating or protecting individuals against IL-1, apoptosis-, IL-18, or IFN-γ-mediated diseases over extended periods of time. The compounds may be employed in such compositions either alone or together with other compounds of this invention in a manner consistent with the conventional utilization of enzyme inhibitors in pharmaceutical compositions. For example, a compound of this invention may be combined with pharmaceutically acceptable adjuvants conventionally employed in vaccines and administered in prophylactically effective amounts to protect individuals over an extended period of time against IL-1-, apoptosis-, IL-18, or IFN-γ-mediated diseases.

The compounds of formula I may also be co-administered with other caspase or ICE inhibitors to increase the effect of therapy or prophylaxis against various IL-1-, apoptosis-, IL-18-, or IFN-γ-mediated diseases.

In addition, the compounds of this invention may be used in combination with either conventional anti-inflammatory agents or with matrix metalloprotease inhibitors, lipoxygenase inhibitors and antagonists of cytokines other than IL-1β.

The compounds of this invention can also be administered in combination with immunomodulators (e.g., bropirimine, anti-human alpha-interferon antibody, IL-2, GM-CSF, methionine enkephalin, interferon-alpha, diethyldithiocarbamate, tumor necrosis factor, naltrexone and EPO), with prostaglandins, or with antiviral agents (e.g., 3TC, polysulfated polysaccharides, ganiclovir, ribavirin, acyclovir, alpha interferon, trimethotrexate and fancyclovir) or prodrugs of these or related compounds to prevent or combat IL-1-mediated disease symptoms such as inflammation.

When the compounds of this invention are administered in combination therapies with other agents, they may be administered sequentially or concurrently to the patient. Alternatively, pharmaceutical or prophylactic compositions according to this invention comprise a combination of a compound of formula I and another therapeutic or prophylactic agent.

The pharmaceutical compositions of this invention may be administered orally, parenterally, by inhalation spray, topically, rectally, nasally, buccally, vaginally or via an implanted reservoir. We prefer oral administration. The pharmaceutical compositions of this invention may contain any conventional non-toxic pharmaceutically-acceptable carriers, adjuvants or vehicles. In some cases, the pH of the formulation may be adjusted with pharmaceutically acceptable acids, bases or buffers to enhance the stability of the formulated compound or its delivery form. The term parenteral as used herein includes subcutaneous, intracutaneous, intravenous, intramuscular, intra-articular, intrasynovial, intrasternal, intrathecal, intralesional and intracranial injection or infusion techniques.

The pharmaceutical compositions may be in the form of a sterile injectable preparation, for example, as a sterile injectable aqueous or oleaginous suspension. This suspension may be formulated according to techniques known in the art using suitable dispersing or wetting agents (such as, for example, Tween 80™) and suspending agents. The sterile injectable preparation may also be a sterile injectable solution or suspension in a non-toxic parenterally-acceptable diluent or solvent, for example, as a solution in 1,3-butanediol. Among the acceptable vehicles and solvents that may be employed are mannitol, water, Ringer's solution and isotonic sodium chloride solution. In addition, sterile, fixed oils are conventionally employed as a solvent or suspending medium. For this purpose, any bland fixed oil may be employed including synthetic mono- or diglycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant, such as those described in Pharmacopeia Helvetica, or a similar alcohol.

The pharmaceutical compositions of this invention may be orally administered in any orally acceptable dosage form including, but not limited to, capsules, tablets, and aqueous suspensions and solutions. In the case of tablets for oral use, carriers which are commonly used include lactose and corn starch. Lubricating agents, such as magnesium stearate, are also typically added. For oral administration in a capsule form, useful diluents include lactose and dried corn starch. When aqueous suspensions and solutions and propylene glycol are administered orally, the active ingredient is combined with emulsifying and suspending agents. If desired, certain sweetening and/or flavoring and/or coloring agents may be added.

The pharmaceutical compositions of this invention may also be administered in the form of suppositories for rectal administration. These compositions can be prepared by mixing a compound of this invention with a suitable non-irritating excipient which is solid at room temperature but liquid at the rectal temperature and therefore will melt in the rectum to release the active components. Such materials include, but are not limited to, cocoa butter, beeswax and polyethylene glycols.

Topical administration of the pharmaceutical compositions of this invention is especially useful when the desired treatment involves areas or organs readily accessible by topical application. For application topically to the skin, the pharmaceutical composition should be formulated with a suitable ointment containing the active components suspended or dissolved in a carrier. Carriers for topical administration of the compounds of this invention include, but are not limited to, mineral oil, liquid petroleum, white petroleum, propylene glycol, polyoxyethylene polyoxypropylene compound, emulsifying wax and water. Alternatively, the pharmaceutical composition can be formulated with a suitable lotion or cream containing the active compound suspended or dissolved in a carrier. Suitable carriers include, but are not limited to, mineral oil, sorbitan monostearate, polysorbate 60, cetyl esters wax, cetearyl alcohol, 2-octyl-dodecanol, benzyl alcohol and water. The pharmaceutical compositions of this invention may also be topically applied to the lower intestinal tract by rectal suppository formulation or in a suitable enema formulation. Topically-administered transdermal patches are also included in this invention.

The pharmaceutical compositions of this invention may be administered by nasal aerosol or inhalation. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other solubilizing or dispersing agents known in the art.

Dosage levels of between about 0.01 and about 100 mg/kg body weight per day, preferably between 0.5 and about 75 mg/kg body weight per day and most preferably between about 1 and 50 mg/kg body weight per day of the active ingredient compound are useful in a monotherapy for the prevention and treatment of IL-1-, apoptosis-, IL-18-, and IFN-γ-mediated diseases, including uveitis, inflammatory diseases, autoimmune diseases, destructive bone disorders, proliferative disorders, infectious diseases, degenerative diseases, necrotic diseases, inflammatory peritonitis, osteoarthritis, acute pancreatitis, chronic pancreatitis, asthma, adult respiratory distress syndrome, glomerulonephritis, rheumatoid arthritis, systemic lupus erythematosus, scleroderma, chronic thyroiditis, Graves' disease, autoimmune gastritis, insulin-dependent diabetes mellitus (Type I), autoimmune hemolytic anemia, autoimmune neutropenia, thrombocytopenia, chronic active hepatitis, myasthenia gravis, inflammatory bowel disease, Crohn's disease, psoriasis, atopic dermatitis, graft vs. host disease, osteoporosis, multiple myeloma-related bone disorder, leukemias and related disorders, myelodysplastic syndrome, acute myelogenous leukemia, chronic myelogenous leukemia, metastatic melanoma, Kaposi's sarcoma, multiple myeloma, sepsis, septic shock, Shigellosis, Alzheimer's disease, Parkinson's disease, cerebral ischemia, myocardial ischemia, myocardial infarction, congestive heart failure, Huntington's disease, atherosclerosis, spinal muscular atrophy, multiple sclerosis, AIDS-related encephalitis, HIV-related encephalitis, aging, alopecia, neurological damage due to stroke, ulcerative colitis, infectious hepatitis, juvenile diabetes, lichenplanus, acute dermatomyositis, eczema, primary cirrhosis, uveitis, Behcet's disease, atopic skin disease, pure red cell aplasia, aplastic anemia, amyotrophic lateral sclerosis, nephrotic syndrome and systemic diseases or diseases with effects localized in the liver or other organs having an inflammatory or apoptotic component caused by excess dietary alcohol intake or viruses, such as HBV, HCV, HGV, yellow fever virus, dengue fever virus, and Japanese encephalitis virus.

Typically, the pharmaceutical compositions of this invention will be administered from about 1 to 5 times per day or alternatively, as a continuous infusion.

Such administration can be used as a chronic or acute therapy. The amount of active ingredient that may be combined with the carrier materials to produce a single dosage form will vary depending upon the host treated and the particular mode of administration. A typical preparation will contain from about 5% to about 95% active compound (w/w). Preferably, such preparations contain from about 20% to about 80% active compound.

When the compositions of this invention comprise a combination of a compound of formula I and one or more additional therapeutic or prophylactic agents, both the compound and the additional agent should be present at dosage levels of between about 10% to 80% of the dosage normally administered in a monotherapy regime.

Upon improvement of a patient's condition, a maintenance dose of a compound, composition or combination of this invention may be administered, if necessary. Subsequently, the dosage or frequency of administration, or both, may be reduced, as a function of the symptoms, to a level at which the improved condition is retained. When the symptoms have been alleviated to the desired level, treatment should cease. Patients may, however, require intermittent treatment on a long-term basis upon any recurrence or disease symptoms.

As the skilled artisan will appreciate, lower or higher doses than those recited above may be required. Specific dosage and treatment regimens for any particular patient will depend upon a variety of factors, including the activity of the specific compound employed, the age, body weight, general health status, sex, diet, time of administration, rate of excretion, drug combination, the severity and course of the disease, and the patient's disposition to the disease and the judgment of the treating physician.

IL-1 or apoptosis mediated diseases which may be treated or prevented by the compounds of this invention include, but are not limited to, inflammatory diseases, autoimmune diseases, proliferative disorders, infectious diseases, and degenerative diseases. The apoptosis-mediated diseases which may be treated or prevented by the compounds of this invention include degenerative diseases.

IL-1 or apoptosis mediated inflammatory diseases which may be treated or prevented include, but are not limited to osteoarthritis, acute pancreatitis, chronic pancreatitis, asthma, and adult respiratory distress syndrome. Preferably the inflammatory disease is osteoarthritis or acute pancreatitis.

IL-1 or apoptosis mediated autoimmune diseases which may be treated or prevented include, but are not limited to, glomerulonephritis, rheumatoid arthritis, systemic lupus erythematosus, scleroderma, chronic thyroiditis, Graves' disease, autoimmune gastritis, insulin-dependent diabetes mellitus (Type I), autoimmune hemolytic anemia, autoimmune neutropenia, thrombocytopenia, chronic active hepatitis, myasthenia gravis, multiple sclerosis, inflammatory bowel disease, Crohn's disease, psoriasis, atopic dermatitis and graft vs. host disease. Preferably the autoimmune disease is rheumatoid arthritis, inflammatory bowel disease, Crohn's disease, psoriasis, or atopic dermatitis.

IL-1 or apoptosis mediated destructive bone disorders which may be treated or prevented include, but are not limited to, osteoporosis and multiple myeloma-related bone disorder.

IL-1 or apoptosis mediated proliferative diseases which may be treated or prevented include, but are not limited to, leukemias and related disorders, such as myelodysplastic syndrome, acute myelogenous leukemia, chronic myelogenous leukemia, metastatic melanoma, Kaposi's sarcoma, and multiple myeloma.

IL-1 or apoptosis mediated infectious diseases which may be treated or prevented include, but are not limited to, sepsis, septic shock, and Shigellosis.

IL-1 or apoptosis mediated degenerative or necrotic diseases which may be treated or prevented by the compounds of this invention include, but are not limited to, Alzheimer's disease, Parkinson's disease, cerebral ischemia, and myocardial ischemia. Preferably, the degenerative disease is Alzheimer's disease.

IL-1 or apoptosis-mediated degenerative diseases which may be treated or prevented by the compounds of this invention include, but are not limited to, Alzheimer's disease, Parkinson's disease, cerebral ischemia, myocardial ischemia, spinal muscular atrophy, multiple sclerosis, AIDS-related encephalitis, HIV-related encephalitis, aging, alopecia, and neurological damage due to stroke.

Other diseases having an inflammatory or apoptotic component may be treated or prevented by the compounds of this invention. Such diseases may be systemic diseases or diseases with effects localized in the liver or other organs and may be caused by, for example, excess dietary alcohol intake or viruses, such as HBV, HCV, HGV, yellow fever virus, dengue fever virus, and Japanese encephalitis virus.

IL-18- or IFN-γ-mediated diseases which may be treated or prevented by the compounds of this invention include, but are not limited to, inflammatory, infectious, autoimmune, proliferative, neurodegenerative and necrotic conditions.

IL-18- or IFN-γ-mediated inflammatory diseases which may be treated or prevented include, but are not limited to osteoarthritis, acute pancreatitis, chronic pancreatitis, asthma, rheumatoid arthritis, inflammatory bowel disease, Crohn's disease, ulcerative collitis, cerebral ischemia, myocardial ischemia and adult respiratory distress syndrome. Preferably, the inflammatory disease is rheumatoid arthritis, ulcerative collitis, Crohn's disease, hepatitis or adult respiratory distress syndrome.

IL-18- or IFN-γ-mediated infectious diseases which may be treated or prevented include, but are not limited to infectious hepatitis, sepsis, septic shock and Shigellosis.

IL-18- or IFN-γ-mediated autoimmune diseases which may be treated or prevented include, but are not limited to glomerulonephritis, systemic lupus erythematosus, scleroderma, chronic thyroiditis, Graves' disease, autoimmune gastritis, insulin-dependent diabetes mellitus (Type I), juvenile diabetes, autoimmune hemolytic anemia, autoimmune neutropenia, thrombocytopenia, myasthenia gravis, multiple sclerosis, psoriasis, lichenplanus, graft vs. host disease, acute dermatomyositis, eczema, primary cirrhosis, hepatitis, uveitis, Behcet's disease, atopic skin disease, pure red cell aplasia, aplastic anemia, amyotrophic lateral sclerosis and nephrotic syndrome. Preferably, the autoimmune disease is glomerulonephritis, insulin-dependent diabetes mellitus (Type I), juvenile diabetes, psoriasis, graft vs. host disease or hepatitis.

More preferred diseases or conditions which may be treated or prevented include rheumatoid arthritis, inflammatory bowel disease, including Crohn's disease and ulcerative colitis, inflammatory peritonitis, amyotrophic lateral sclerosis, septic shock, pancreatitis, traumatic brain injury, organ transplant rejection, osteoporosis, osteoarthritis, asthma, uveitis, psoriasis, Alzheimer's disease, myocardial infarction, congestive heart failure, Huntington's disease, atherosclerosis, atopic dermatitis, or leukemias and related disorders, such as myelodysplastic syndrome or multiple myeloma.

Accordingly, one embodiment of this invention provides a method for treating or preventing an IL-1 or apoptosis mediated disease in a subject comprising the step of administering to the subject any compound, pharmaceutical composition, or combination described herein and a pharmaceutically acceptable carrier.

Another embodiment of this invention provides a method for decreasing IL-18 production in a subject comprising the step of administering to the subject any compound, pharmaceutical composition, or combination described herein and a pharmaceutically acceptable carrier.

Yet another embodiment of this invention provides a method for decreasing IFN-γ production in a subject comprising the step of administering to the subject any compound, pharmaceutical composition, or combination described herein and a pharmaceutically acceptable carrier.

Although this invention focuses on the use of the compounds disclosed herein for preventing and treating IL-1, apoptosis-, IL-18, and IFN-□-mediated diseases, the compounds of this invention can also be used as inhibitory agents for other cysteine proteases.

The compounds of this invention are also useful as commercial reagents which effectively bind to caspases or other cysteine proteases including, but not limited to ICE. As commercial reagents, the compounds of this invention, and their derivatives, may be used to block proteolysis of a target peptide in biochemical or cellular assays for ICE and ICE homologs or may be derivatized to bind to a stable resin as a tethered substrate for affinity chromatography applications. These and other uses which characterize commercial cysteine protease inhibitors will be evident to those of ordinary skill in the art.

In order that this invention be more fully understood, the following examples are set forth. These examples are for the purpose of illustration only and are not to be construed as limiting the scope of the invention in any way.

Synthetic Examples

Preparation of 1-[2-(4-amino-3-chloro-benzoylamino)-3,3-dimethyl-butyryl]-pyrrolidine-2-carboxylic acid (2-ethoxy-5-oxo-tetrahydro-furan-3-yl)-amide (I-A)

2-Benzyloxycarbonylamino-3,3-dimethyl-butyric acid (2)

To a solution of L-tert-leucine (1) (50.0 g, 38.0 mmol) and $NaHCO_3$ (96.0 g, 114 mmol) in ice (500 g) and water (500 ml) was added benzyl chloroformate (65.0 ml, 74.0 mmol) and the reaction stirred at 0° C. for 3 hours then at room temperature for 18 hours. 0.1N $Na_2CO_3$ was added until the oily layer dissolved and the solution was washed with 10% EtOAc in hexanes (2×500 ml). The iced aqueous phase was acidified to pH 1 using 12N HCl then extracted using EtOAc (3×350 ml). The combined organic extracts were dried over $Na_2SO_4$, filtered and evaporated to give the title compound as a colorless oil (82.4 g, 81.5% yield): $^1$H-NMR (500 MHz, $CDCl_3$) δ1.02 (s, 9H), 4.22 (d, 1H), 5.10-5.14 (m, 2H), 5.31 (d, 1H), 7.26-7.37 (m, 5H).

1-(2-Benzyloxycarbonylamino-3,3-dimethyl-butyryl)-pyrrolidine-2-carboxylic acid tert-butyl ester (3)

To a solution of 2 (6.01 g, 2.0 mmol) in $CH_2Cl_2$ (30 ml) and anhydrous DMF (dimethylformamide) (10 ml) at 0° C. was added HOBT (3.16 g, 2.0 mmol), EDC (1-(3-dimethylaminopropyl-3-ethyl-carbodiimide hydrochloride) (7.19 g, 4.0 mmol) and L-proline-tert-butyl ester (4.22 g, 2.0 mmol). The solution was stirred at 0° C. for 10 minutes, then at room temperature for 5 hours. The solvents were evaporated in-vacuo and the resulting oil dissolved in EtOAc which was washed with $H_2O$ (3×200 ml) and brine (200 ml). The organic phase was dried over anhydrous $Na_2SO_4$, filtered and evaporated to give the crude product. Flash chromatography on silica gel using hexanes/EtOAc (95/5 to 80/20%) afforded the title compound as a colorless oil (8.30 g, 87.5% yield): 1H-NMR (500 MHz, $CDCl_3$) δ1.04 (s, 9H), 1.45 (s, 9H), 1.89-1.96 (m, 2H), 2.02-2.05 (m, 1H), 2.18-2.22 (m, 1H), 3.65-3.69 (m, 1H), 3.79-3.82 (m, 1H), 4.34-4.37 (m, 2H), 5.03-5.19 (m, 2H), 5.53 (d, 1H), 7.26-7.38 (5H).

Synthesis of 1-[2-(4-amino-3-chloro-benzoylamino)-3,3-dimethyl-butyryl]-pyrrolidine-2-carboxylic acid tert-butyl ester (4)

To a solution of 3 (19.0 g, 45.4 mmol) in MeOH (200 mL) was added 10% activated Pd on C (2.0 g) in EtOAc (50 mL) and the reaction stirred under $H_2$ for 18 hours. The solution was filtered through Celite and the solvent evaporated to yield a viscous, colorless oil. The free amine was dissolved in dry $CH_2Cl_2$/DMF (2:1, 120 mL), the solution cooled to 0° C. and 4-amino-3-chlorobenzoic acid (7.79 g, 45.4 mmol) and DIPEA (7.90 mL, 45.4 mmol) were added. The reaction was stirred for 10 minutes, then EDC (11.32 g, 59.1 mmol) was added. The mixture was stirred at 0° C. for 30 minutes then at room temperature for 18 hours. The solution was diluted with EtOAc (300 mL), washed with 0.5N $NaHSO_4$ (2×250 mL), 10% $NaHCO_3$ (2×250 mL), saturated NaCl (150 mL), dried over $MgSO_4$, and evaporated to dryness. Flash column chromatography on silica gel using $CH_2Cl_2$/MeOH, (99/1 to 98/2%) yielded the title compound as a white solid (19.25 g, 97% yield): $^1$H-NMR (500 MHz, $CDCl_3$) δ 1.12 (s, 9H), 1.48 (s, 9H), 1.85-1.99 (m, 2H), 2.01-2.13 (m, 1H), 2.18-2.29 (m, 1H), 3.63-3.73 (m, 1H), 3.84-3.93 (m, 1H), 4.30-4.41 (m, 1H), 4.86 (d, 1H), 6.73 (d, 1H), 7.51 (d, 1H), 7.73 (s, 1H). Analytical HPLC (cyano column): 12.59 min. LC-MS (ES+) m/e=438.5 (M+H).

Synthesis of 1-[2-(4-amino-3-chloro-benzoylamino)-3,3-dimethyl-butyryl]-pyrrolidine-2-carboxylic acid (5)

To a solution of 4 (15.9 g, 36.3 mmol) in $CH_2Cl_2$ (30 mL) was added TFA (trifluoroacetic acetic acid)(30 mL) and the solution stirred at room temperature for 3 hours under $N_2$. The reaction was transferred to a beaker (1 L) and diluted with $CH_2Cl_2$ (60 mL). To the solution at 0° C. was added solid $NaHCO_3$ (39 g, 46 mmol) and stirred for 15 minutes before partitioning between EtOAc (300 mL) and $H_2O$ (300 mL). After extraction the aqueous layer was acidified to pH 4-5 and extracted with EtOAc. The organic layer was dried ($MgSO_4$) and evaporated to dryness to give 5 as a white solid (14.0 g, quantitative yield): $^1$H-NMR (500 MHz, $CDCl_3$) δ1.08 (s, 9H), 1.97-2.22 (m, 3H), 2.29-2.41 (m, 1H), 3.71-3.78 (m, 1H), 3.90-3.98 (m, 1H), 4.55-4.62 (m, 1H), 4.86 (d, 1H), 6.64 (d, 1H), 6.74 (d, 1H), 7.53 (d, 1H), 7.74 (s, 1H). Analytical HPLC (cyano column): 8.24 min. LC-MS (ES+) m/e=382.4 (M+H).

Synthesis of 1-[2-(4-amino-3-chloro-benzoylamino)-3,3-dimethyl-butyryl]-pyrrolidine-2-carboxylic acid (2-ethoxy-5-oxo-tetrahydro-furan-3-yl)-amide (I-A)

To a solution of 6 (5.05 g, 22.0 mmol) in $CH_2Cl_2$ (50 mL) at 0° C. was added 1,3-dimethylbarbituric acid (DMBA) (3.78 g, 24.2 mmol) and $Pd(PPh_3)_4$(0.15 g, 0.13 mmol). After 10 minutes, a solution of 5 (8.40 g, 22.0 mmol) in DMF (25 mL) was added followed by diisopropylethylamine (DIPEA) (7.66 mL, 44.1 mmol), (2.98 g, 22.0 mmol) and EDC (5.06 g, 26.4 mmol). The solution was stirred at 0° C. for 10 minutes then at room temperature for 18 hours. The reaction was diluted with EtOAc (200 mL), washed with 0.5N $NaHSO_4$ (2×200 mL), 10% $NaHCO_3$ (2×200 mL), saturated NaCl (1×150 mL), dried over anhydrous $MgSO_4$, and evaporated to dryness. Flash column chromatography on silica gel using $CH_2Cl_2$/MeOH, (99/1 to 98/2%) afforded the title compound as a white solid (11.20 g, 77% yield): $^1$H-NMR (500 MHz, $CDCl_3$) δ 1.08 (s, 9H), 1.27 (t, 3H), 1.85-1.99 (m, 1H), 2.00-2.06 (m. 1H), 2.07-2.18 (m, 1H), 2.32-2.48 (m, 2H), 2.78-2.89 (m, 1H), 3.62-3.76 (m, 2H), 3.82-3.96 (m, 2H), 4.39 (s, 1H), 4.54-4.60 (m, 1H), 4.62-4.76 (m, 1H), 4.85 (d, 1H), 6.57 (d, 1H), 6.73 (d, 1H), 7.38 (d, 1H), 7.49 (d, 1H), 7.72 (s, 1H). Analytical HPLC (cyano column): 13.10 min. LC-MS (ES$^+$) m/e=509.4 (M+H), m.p.=96-99° C.

Oral Pharmacokinetic Studies

Male Sprague-Dawley rats (Harlan, Indianapolis, Ind., 300-350 g) were anesthetized by an intramuscular injection of ketamine/rompun mixture. A PE-50 cannula was inserted in the right carotid artery for arterial blood sampling. The rats were allowed to recover from surgery overnight (16 hours) prior to being used in the study. Test compounds were administered orally at 50 mg/kg 100% propylene glycol (PG) at a dose volume of 10 mL/kg. Blood samples (~0.30 mL) were removed at 0.25, 0.50, 1.0, 1.5, 2, 3, 4, 6, and 8 hours post-dose, plasma separated by centrifugation and stored at −80° C. pending analysis. Quantification of the plasma samples was conducted using a gradient HPLC/MS/MS similar to the one detailed below:

HPLC/MS/MS Method for the Quantitation of ICE Inhibitors in Rat Plasma

Sample Preparation
1. 100 µl of plasma are aliquotted into Ependorf centrifuge vials.
2. An equal volume of acetonitrile is added to the plasma to precipitate plasma proteins.
3. Samples are vortexed for 2 minutes, and centrifuged at 14,000 rpms for 3 minutes.
4. 100 µl of the supernatant is loaded into 12 mm HPLC liquid sampler vials.
5. A 20 µl addition of external standard is added to the 100 ul aliquot to monitor variation in instrumental response.
6. 10 µl of sample is injected for analysis via the mass spectrometer.

HPLC Instrumental Parameters
HPLC: Hewlett Packard HP1100 Binary Solvent Delivery System.
HPLC Gradient Conditions
A=$H_2O$ 0.2% Formic Acid
B=Acetonitrile 0.2% Formic Acid
Mobile Phase

| Time (min) | % A | % B |
|---|---|---|
| 0 | 100 | 0 |
| 2 | 100 | 0 |
| 5 | 0 | 100 |
| 11 | 0 | 100 |
| 11.5 | 100 | 0 |
| 15 | 100 | 0 |

HPLC Analytical Column: Keystone Phenyl-1 Hypersil 2.0× 100 mm, 5µ 120 Å pore pore size, P/N#105-36-2
Injection Volume: 10 µl
Flow Rate: 0.20 mL/min.
Mass Spectrometry Instrumental Parameters
Instrument: Micromass Quattro Ultima, Tandem Mass Spectrometer
Ionization Technique: Orthogonal spray (ESI)
Polarity: Positive
Dwell Time: 300 msec
Pause Time: 5 msec
Scan time: 0.9 sec
Scan Mode: MRM (Multiple Reaction Monitoring)
Ions/Transitions: For compound I-A m/z509.1-243.1
For compound II m/z481.1-215.1

Pharmacokinetic Parameters

Pharmacokinetic analysis of these plasma concentration data was conducted using noncompartmental methods. The area under the curve ($AUC_{(0-t)}$) was estimated from time zero to the last measured time point using the linear trapezoidal rule. The rate of elimination (ke) was estimated by log-linear regression from the terminal phase of the plasma concentration-time curves. Area under the tail of the curve was estimated as the ratio of the last measured concentration to ke. The area under the curve from time zero to infinity ($AUC(0-\infty)$) was obtained by addition of the area under the tail to AUC(O-t). Elimination half-life was estimated as 0.693/ke. The observed values for the peak plasma concentration (Cmax) were recorded.

TABLE 1

Oral Pharmacokinetic Data

| Example | Cmax (µg/mL) | AUC (µgXh/mL) | t 1/2 (hrs) |
|---|---|---|---|
| 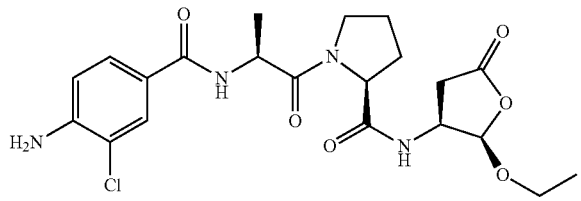 Compound A | 1.8 | 2.18 | 2.9 |
| 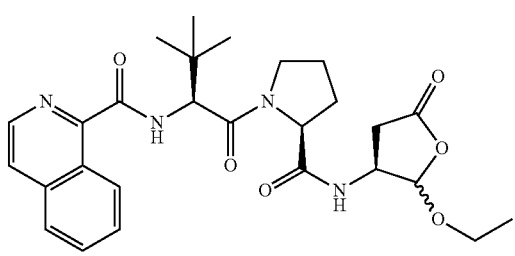 Compound B | 0.51 | 1.35 | 0.25 |

TABLE 1-continued

Oral Pharmacokinetic Data

| Example | Cmax (µg/mL) | AUC (µgXh/mL) | t 1/2 (hrs) |
|---|---|---|---|
| 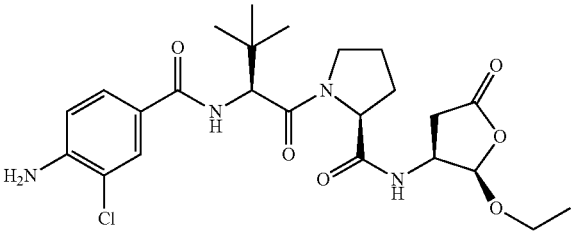

Compound I | 4.27 | 11.7 | 2.5 |

Table 1 above compares the pharmacokietic values of compound I with compounds A and B that are closely related in structure. As can be seen from the data, Cmax and AUC are much higher for compound I than for the other two compounds.

While we have described a number of embodiments of this invention, it is apparent that our basic constructions may be altered to provide other embodiments that utilize the products and processes of this invention.

We claim:

1. A topical formulation comprising a compound of formula I, or a pharmaceutically acceptable salt thereof:

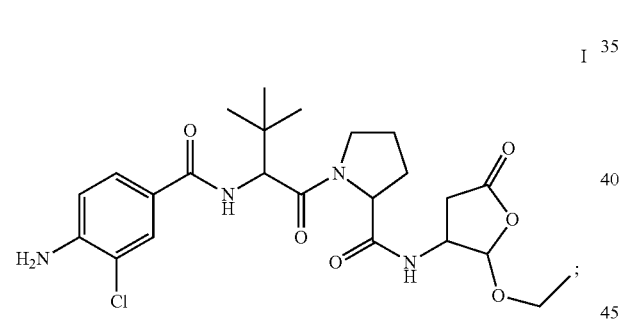

I and a pharmaceutically acceptable carrier, adjuvant, or vehicle;
wherein the pharmaceutically acceptable carrier, adjuvant, or vehicle is a mineral oil, liquid petroleum, white petroleum, propylene glycol, polyoxyethylene polyoxypropylene compound, emulsifying wax, sorbitan monostearate, polysorbate 60, cetyl esters wax, cetearyl alcohol, 2-octyldodecanol, benzyl alcohol, water, or a combination thereof.

2. The topical formulation of claim 1, wherein the topical formulation comprises a therapeutically effective amount of the compound of formula I, or the pharmaceutically acceptable salt thereof.

3. The topical formulation of claim 1, wherein the topical formulation is an ointment.

4. The topical formulation of claim 1, wherein the topical formulation is a cream or a lotion.

5. The topical formulation of claim 1, wherein the compound of formula I, or pharmaceutically acceptable salt thereof, is in an amount of 5% w/w to 95% w/w of the topical formulation.

6. The topical formulation of claim 1, further comprising an additional agent, wherein the additional agent is an anti-inflammatory agent, a matrix metalloprotease inhibitor, a lipoxygenase inhibitor, a cytokine antagonist, an immunosuppressant, an anti-cancer agent, an anti-viral agent, a cytokine, a growth factor, an immunomodulator, a prostaglandin, an anti-vascular hyperproliferation compound, a pharmaceutically acceptable adjuvant, or a combination thereof.

7. A topical formulation comprising a compound of formula I:

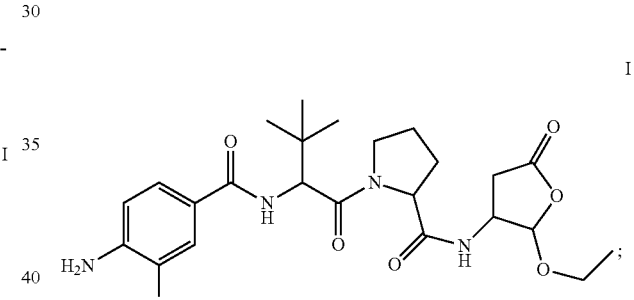

I and a pharmaceutically acceptable carrier, adjuvant, or vehicle;
wherein the pharmaceutically acceptable carrier, adjuvant, or vehicle is a mineral oil, liquid petroleum, white petroleum, propylene glycol, polyoxyethylene polyoxypropylene compound, emulsifying wax, sorbitan monostearate, polysorbate 60, cetyl esters wax, cetearyl alcohol, 2-octyldodecanol, benzyl alcohol, water, or a combination thereof.

8. A topical formulation comprising a compound of formula I-A:

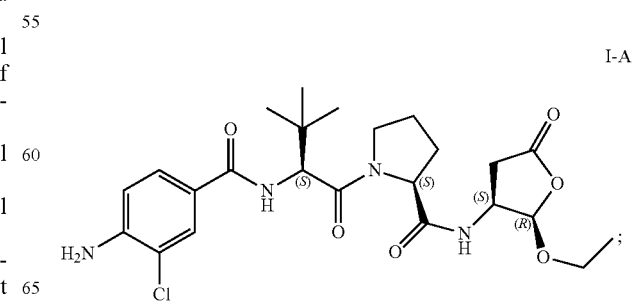

I-A and a pharmaceutically acceptable carrier, adjuvant, or vehicle.

9. A topical formulation comprising a compound of formula I-B:

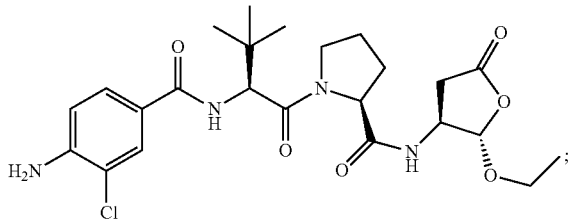

and a pharmaceutically acceptable carrier, adjuvant, or vehicle.

10. A method of treating a disease in a subject in need thereof, comprising the step of administering to said subject a pharmaceutical composition comprising a compound of formula I, or a pharmaceutically acceptable salt thereof:

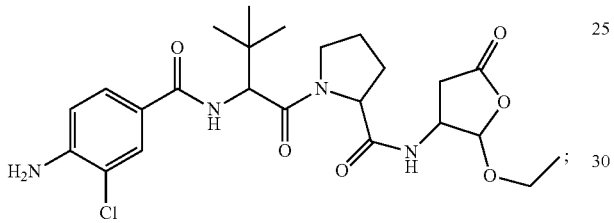

and a pharmaceutically acceptable carrier, adjuvant, or vehicle, wherein the disease is atopic dermatitis, acute dermatomyositis, eczema, metastatic melanoma, or a combination thereof.

11. The method of claim 10, wherein the pharmaceutical composition comprises a therapeutically effective amount of the compound of formula I, or the pharmaceutically acceptable salt thereof.

12. The method of claim 10, wherein the pharmaceutical composition is administered one to five times a day.

13. The method of claim 10, wherein the compound of formula I, or pharmaceutically acceptable salt thereof, is in an amount of 5% w/w to 95% w/w of the pharmaceutical composition.

14. The method of claim 10, wherein the pharmaceutical composition is administered in combination with an additional agent, and wherein the additional agent is an anti-inflammatory agent, a matrix metalloprotease inhibitor, a lipoxygenase inhibitor, a cytokine antagonist, an immunosuppressant, an anti-cancer agent, an anti-viral agent, a cytokine, a growth factor, an immunomodulator, a prostaglandin, an anti-vascular hyperproliferation compound, a pharmaceutically acceptable adjuvant, or a combination thereof.

15. The method of claim 10, wherein the pharmaceutical composition further comprises an additional agent, and wherein the additional agent is an anti-inflammatory agent, a matrix metalloprotease inhibitor, a lipoxygenase inhibitor, a cytokine antagonist, an immunosuppressant, an anti-cancer agent, an anti-viral agent, a cytokine, a growth factor, an immunomodulator, a prostaglandin, an anti-vascular hyperproliferation compound, a pharmaceutically acceptable adjuvant, or a combination thereof.

16. The method of claim 10, wherein the pharmaceutical composition is a topical composition.

17. The method of claim 16, wherein the topical composition is an ointment, a cream, or a lotion.

18. A method of treating a disease in a subject in need thereof, comprising the step of administering to said subject a pharmaceutical composition comprising a compound of formula I:

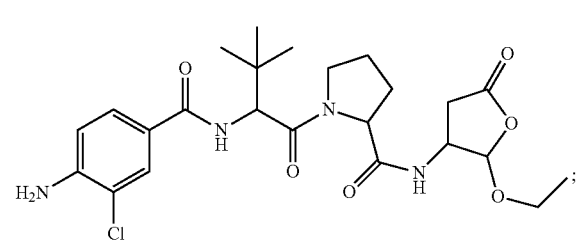

and a pharmaceutically acceptable carrier, adjuvant, or vehicle, wherein the disease is atopic dermatitis, acute dermatomyositis, eczema, metastatic melanoma, or a combination thereof.

19. A method of treating atopic dermatitis in a subject in need thereof, comprising the step of administering to said subject a pharmaceutical composition comprising a compound of formula I, or a pharmaceutically acceptable salt thereof:

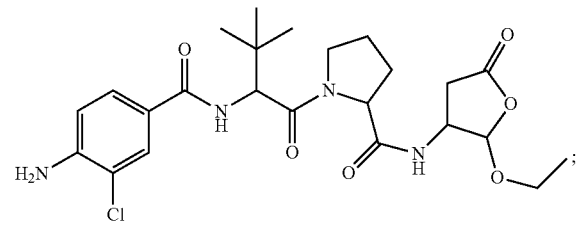

and a pharmaceutically acceptable carrier, adjuvant, or vehicle.

20. The method of claim 19, wherein the pharmaceutical composition comprises a therapeutically effective amount of the compound of formula I, or the pharmaceutically acceptable salt thereof.

21. The method of claim 19, wherein the pharmaceutical composition is administered one to five times a day.

22. The method of claim 19, wherein the compound of formula I, or pharmaceutically acceptable salt thereof, is in an amount of 5% w/w to 95% w/w of the pharmaceutical composition.

23. The method of claim 19, wherein the pharmaceutical composition is a topical composition.

24. The method of claim 23, wherein the topical composition is an ointment, a cream or a lotion.

25. The method of claim 19, wherein the pharmaceutical composition is administered in combination with an additional agent, and wherein the additional agent is an anti-inflammatory agent, a matrix metalloprotease inhibitor, a lipoxygenase inhibitor, a cytokine antagonist, an immunosuppressant, an anti-cancer agent, an anti-viral agent, a cytokine, a growth factor, an immunomodulator, a prostaglandin, an anti-vascular hyperproliferation compound, a pharmaceutically acceptable adjuvant, or a combination thereof.

26. The method of claim 19, wherein the pharmaceutical composition further comprises an additional agent, and wherein the additional agent is an anti-inflammatory agent, a matrix metalloprotease inhibitor, a lipoxygenase inhibitor, a cytokine antagonist, an immunosuppressant, an anti-cancer agent, an anti-viral agent, a cytokine, a growth factor, an immunomodulator, a prostaglandin, an anti-vascular hyperproliferation compound, a pharmaceutically acceptable adjuvant, or a combination thereof.

27. A method of treating atopic dermatitis in a subject in need thereof, comprising the step of administering to said subject a pharmaceutical composition comprising a compound of formula I:

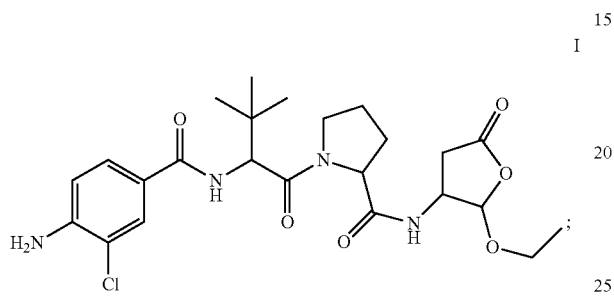

and a pharmaceutically acceptable carrier, adjuvant, or vehicle.

* * * * *